United States Patent
Anderson

(10) Patent No.: US 7,165,970 B2
(45) Date of Patent: Jan. 23, 2007

(54) DENTAL INSTRUMENT

(75) Inventor: Robert Anderson, Coopersville, MI (US)

(73) Assignee: Garrison Dental Solutions, Inc., Spring Lake, MI (US)

( * ) Notice: Subject to any disclaimer, the term of this patent is extended or adjusted under 35 U.S.C. 154(b) by 0 days.

(21) Appl. No.: 11/068,367

(22) Filed: Feb. 28, 2005

(65) Prior Publication Data

US 2005/0191598 A1 Sep. 1, 2005

Related U.S. Application Data

(60) Provisional application No. 60/548,926, filed on Mar. 1, 2004.

(51) Int. Cl.
*A61C 3/14* (2006.01)
*A61C 5/12* (2006.01)

(52) U.S. Cl. .................. 433/159; 433/138; 433/155

(58) Field of Classification Search .............. 433/4, 433/138, 139, 153, 156, 157, 159, 160
See application file for complete search history.

(56) References Cited

U.S. PATENT DOCUMENTS

| | | | | |
|---|---|---|---|---|
| 315,706 A | * | 4/1885 | Brewer et al. | 433/159 |
| 1,336,746 A | * | 4/1920 | Ivory | 433/139 |
| 1,349,767 A | | 8/1920 | Ivory | |
| 1,438,975 A | * | 12/1922 | Wiggins | 433/159 |
| 6,345,983 B1 | * | 2/2002 | Godfrey | 433/159 |

\* cited by examiner

*Primary Examiner*—Cary E. O'Connor
(74) *Attorney, Agent, or Firm*—Van Dyke, Gardner, Linn & Burkhart, LLP

(57) ABSTRACT

A dental instrument includes a first arm, a second arm, which is pivotally coupled to the first arm about a pivot axis, and a spring. The first and second arms are pivotal with respect to each other in a plane generally orthogonal to the pivot axis. Each of the arms has a proximal portion, a medial portion, and a distal portion, with the proximal portions defining hand grip portions, and with the arms being pivotally connected at their medial portions. The spring biases the distal portions of the arms toward each other. Each of the distal portions comprises a first portion and a prong portion depending from the first portion. The prong portions comprise back-to-back generally C-shaped portions and spaced apart tines. The C-shaped portions define a pair of seats, with the tines depending from the seats and having spaced apart distal ends adapted for engaging a rubber-dam clamp, and the seats providing contacts for a dental retaining ring.

21 Claims, 23 Drawing Sheets

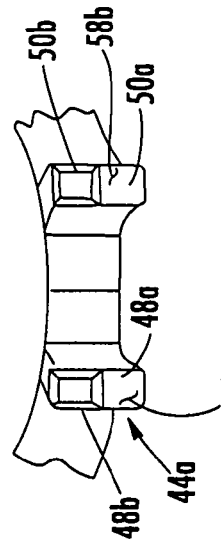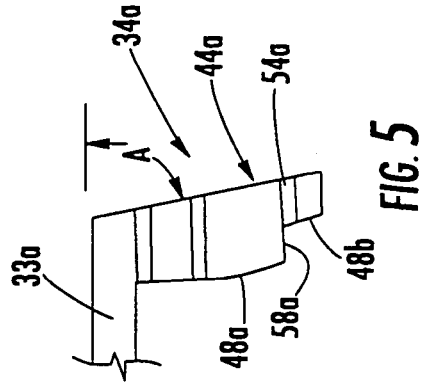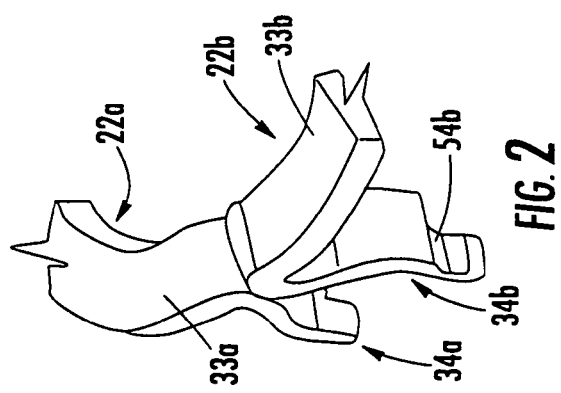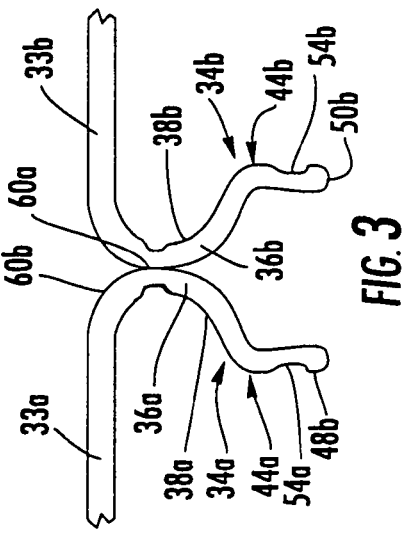

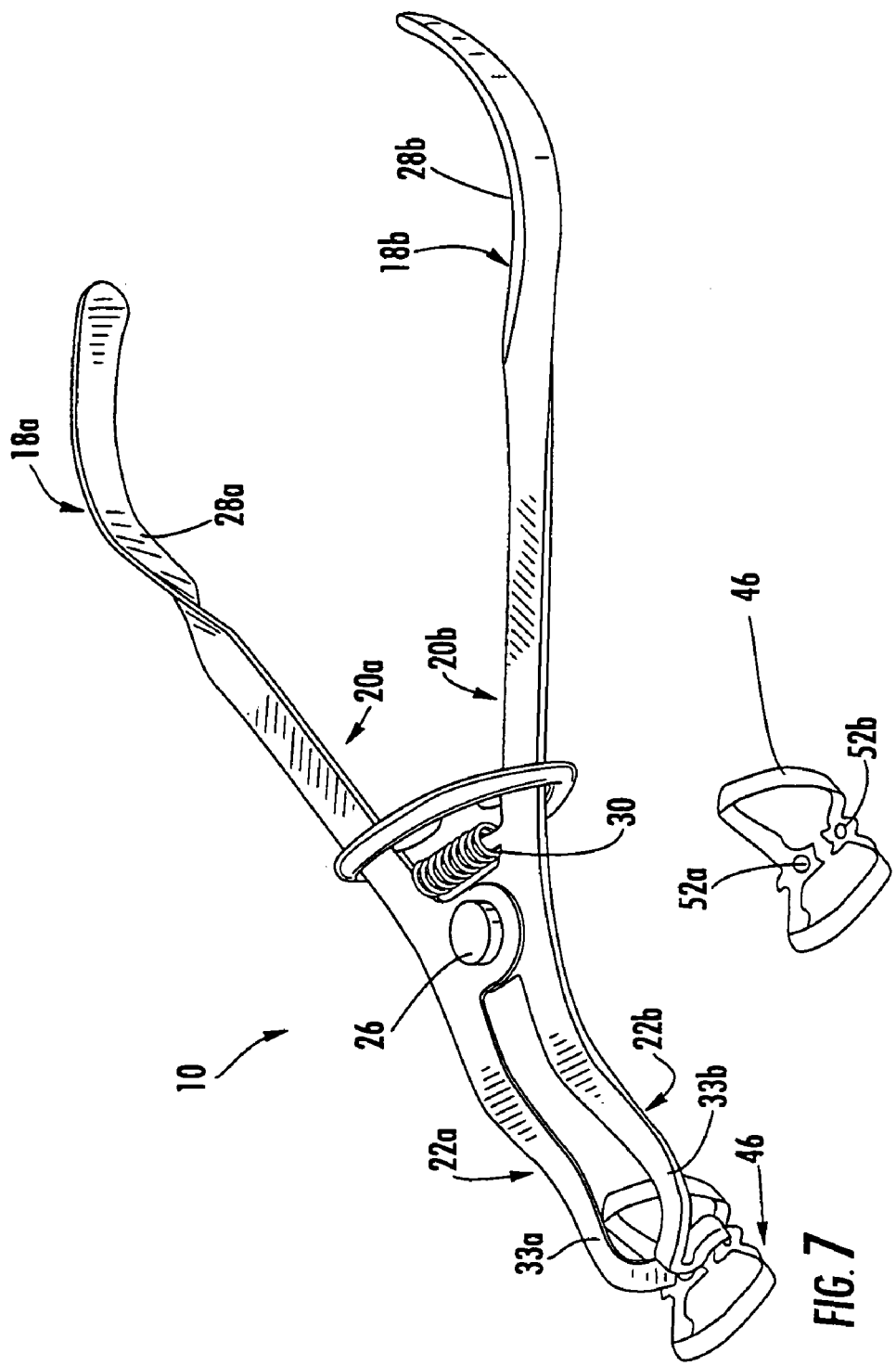

DENTAL INSTRUMENT

This Application claims the benefit of and priority from U.S. provisional Pat. Application Ser. No. 60/548,926, filed Mar. 1, 2004, entitled DENTAL INSTRUMENT by Applicant Robert Anderson, which is incorporated by reference in its entirety herein.

TECHNICAL FIELD AND BACKGROUND OF THE INVENTION

The present invention relates to a dental instrument and, more particularly, to a dental instrument that can be used to place a rubber-dam clamp in a patient's mouth and, further, that can be used to place a retaining ring around a tooth for a sectional matrix system.

A rubber-dam and rubber-dam clamp are used to isolate the field of operation on a tooth from saliva and blood, and to ease removal and filling of material. In addition, the dam prevents the filling material, such as chemicals (bonding agents, etchings, amalgams, and composite material), from coming in contact with the mucus membranes and throat.

The procedure for placing a rubber-dam is to first punch a hole in the rubber-dam material and then place a frame around the rubber-dam material. The hole in the dam is lined up with the tooth or teeth to be isolated. The rubber-dam material is then pushed around the tooth or teeth until it is seated against the gingival tissue. A rubber-dam clamp is then placed on a tooth with a pair of rubber-dam clamp forceps to secure the rubber-dam material from raising up or coming off the patient's tooth or teeth. This procedure is used both in general dentistry as well as endodontic and periodontal procedures where isolation may be needed.

Ring and sectional matrix systems have been used since the 1980's when composite restorations (white fillings) started to become popular. A composite restoration is a tooth color filling material that hardens when a certain wavelength of light comes into contact with the material. The ring of the sectional matrix system provides the force necessary to separate the teeth to accommodate the shrinkage that occurs in all composite materials when they harden. Isolation is extremely important when performing a composite restoration because foreign materials, such as saliva, blood, tooth particles, amalgam and/or composite material, may get into the composite restoration and greatly hamper the success of the restoration. When compromised by foreign material, the bonding and sheer strength of the composite material may be reduced and sensitivity to the patient's tooth will be increased. Hence, the overall success of the composite restoration may be reduced. Therefore, it is imperative for a dentist to isolate the tooth being restored when performing composite restoration, which isolation is best achieved using a rubber-dam.

Today, many dentists are performing composite restorations for their patients and are using a ring and sectional matrix system. When these systems are used with a rubber-dam, the forceps that a dentist uses for placing a rubber-dam clamp are sometimes used for placing the rings when performing the composite amalgam restoration (FIG. 30). However, when using a rubber-dam clamp forceps for placing a ring into the interproximal space of a restoration, the rubber-dam clamp forceps do not open far enough for certain ring systems. In addition, when placing the ring, the lower end of the forceps can get entangled or interfere with the dam and/or a previously placed ring (as best appreciated from FIG. 30). Two rings are often used, for example, when repairing both interproximal areas of a tooth. Further, the ring will often not stay in the proper position for placement between the teeth because it may have a tendency to rock or rotate up or down between the forceps' arms. As a result, there is a risk that the ring will spring off the forceps. This later situation could result in the patient swallowing a ring if the rubber-dam is not properly placed before starting the restoration.

Consequently, there is a need for a dental instrument that permits proper placement of both a rubber-dam clamp and a ring of a sectional matrix system, preferably, with a single dental apparatus.

SUMMARY OF THE INVENTION

The present invention provides a dental instrument that can be used to both place a rubber-dam clamp and to place a ring for a sectional matrix system. The dental instrument is adapted to capture most ring systems, if not all ring systems, used in the field of dentistry, along with the ability to secure and place a rubber-dam clamp about a tooth to secure a rubber-dam in place. Furthermore, the dental instrument is configured to allow the tines of the instrument to avoid the patient's teeth when placing the ring and/or rubber-dam clamp and, further, to avoid entanglement with a previously positioned ring or the rubber-dam itself.

In one form of the invention, a dental instrument includes a first arm and a second arm, which is pivotally coupled to the first arm about a pivot axis. The first and said second arms are pivotally coupled at their medial portions and are pivotable with respect to each other in a plane that is orthogonal to the pivot axis. Each of the arms has a proximal portion, a medial portion, and a distal portion. The proximal portions define handgrip portions. In the instrument also includes a spring that biases the distal portions of the arms toward each other. Each of the distal portions comprises a first portion and a prong portion depending from the first portion. The prong portions comprise back-to-back generally C-shaped portions and spaced apart tines. The C-shaped portions define a pair of seats, with the tines depending from the seats and having spaced apart distal ends adapted for engaging a rubber-dam clamp, with the seats providing contacts for a dental retaining ring.

In one aspect, each of the tines has an upper portion with a first width and a lower portion with a second width, with the second widths being smaller than the first widths wherein the lower portions are sized to insert into openings of a rubber-dam clamp.

In a further aspect, the tines each have a groove between the upper portions and the lower portions. The grooves in the tines provide securement of the rubber dam clamp to the instrument, when the tines are inserted into the rubber-dam clamp.

In another aspect, the tines are non-orthogonal with respect to the plane in which the arms pivot. For example, the tines may be angled forward of said first portions relative to said medial portions in a range of 96° to 104° with respect to the plane.

In other aspects, the first portions of the distal portions are offset from the plane. For example, the first portions of the distal portions may extend in a second plane, which is generally parallel to the first plane. In addition, the first portions may comprise arcuate portions. Furthermore, the first portions preferably include planar lower surfaces, which provide additional stability to the dental retaining ring when captured by the distal portions of the dental instrument.

In another form of the invention, a dental instrument includes a first arm and a second arm, which is pivotally connected to the first arm about a pivot axis. Each of the arms includes a proximal portion, a medial portion, and a distal portion. The proximal portions define handgrip portions. The arms are pivotally interconnected at their respective medial portions such that the arms are pivotal with respect to each other in a plane that is generally orthogonal to the pivot axis. The dental instrument also includes a spring that generates a biasing force to urge the distal portions of the arms towards each other. Each of the distal portions includes a prong portion that includes a first portion and a second portion. The first portion is adapted to capture and secure a portion of a dental retaining ring therein. The second portion extends from the first portion and includes a distal end that is adapted to engage a rubber-dam clamp.

In one aspect, the distal ends are spaced apart when the distal portions of the arms abut.

In another aspect, each of the first portions comprises an arcuate portion, which define seats for capturing portions of the dental retaining ring therein. In addition, the distal ends may be aligned with the ends of the seats. Alternately, the distal ends may be spaced inwardly of the ends of the seats.

In another aspect, each of the arcuate portions includes an apex, with the apexes contacting each other when the biasing force is unopposed and the distal portions of the arms are urged toward each other by the spring.

According to yet other aspects, the second portions comprise tines. Each tine includes an upper portion with a first width and a lower portion having a second width, with the second widths being smaller than said first widths wherein the lower portions are sized to insert into openings of a rubber-dam clamp.

In further aspects, the tines are non-orthogonal with respect to the plane in which the arms pivot. For example, the tines may be angled forward in a range of 96° to 104° with respect to the plane in which the arms are pivotally connected.

In other aspects, the prongs have a length in a range of about 8 to 10 mm, more preferably in a range of about 7 to 9 mm to thereby minimize the contact of the prongs with the teeth or gums of the patient.

According to another aspect, the upper portions extend in a plane that is generally parallel to the plane in which the arms pivot. For example, the upper portions may comprise arcuate portions.

In yet another aspect, at least a portion of each of the second portions of the prong portions are removable. Alternately, or in addition, at least a portion of the second portions of the prong portions are pivotally mounted to the distal portions.

According to another form of the invention, a dental instrument includes a first arm, a second arm that is pivotally coupled to the first arm about a pivot axis. The first and second arms are pivotal with respect to each other in a plane generally orthogonal to the pivot axis. Each of the arms has a proximal portion, a medial portion, and a distal portion, with the proximal portions defining hand grip portions. The arms are pivotally coupled at their respective medial portions. The instrument also includes a spring that generates a biasing force to urge the distal portions toward each other. Each of the distal portions is adapted to capture an arm of a retaining ring therein and has tines extending therefrom. Each of the tines is adapted to engage a rubber-dam clamp. Further, each of the second portions is angled forward of the first portion in a direction away from its respective medial portion wherein the tines are non-parallel to the pivot axis.

For example, the second portions may be angled with respect to the first portions in a range of about 96° to 104° or in a range of about 98° to 102°.

In one aspect, the second portions comprise arcuate portions, with each of the arcuate portions being configured to capture an arm of a retaining ring therein. When the biasing force is unopposed, the distal portions are urged toward each other but the tines are spaced apart.

In further aspects, each of the arcuate portions has an end. The tines are positioned inwardly of the ends of the arcuate portions.

Alternately, the tines extend from the ends and are aligned with the ends of the arcuate portions.

Accordingly, the present invention combines a rubber-dam clamp with a dental retaining ring instrument that is configured so that it can be used to place a rubber-dam clamp and, further, to place one or more retaining rings into the interproximal area of a tooth.

These and other objects, advantages, purposes, and features of the invention will become more apparent from the study of the following description taken in conjunction with the drawings.

DETAILED DESCRIPTION OF THE DRAWINGS

FIG. 2 is an enlarged fragmentary perspective view of the ends of the dental instruments of FIG. 1;

FIG. 3 is an elevation view of the ends of the dental instrument illustrated in FIG. 2;

FIG. 4 is a bottom plan view of the ends of the dental instrument of FIG. 3;

FIG. 5 is a side elevation view of the ends of FIG. 3;

FIG. 6 is a respective view of a rubber-dam clamp;

FIG. 7 is a perspective view of the dental instrument of FIG. 1 operating on the rubber-dam clamp of FIG. 6;

DETAILED DESCRIPTION OF THE PREFERRED EMBODIMENTS

Figure 1:
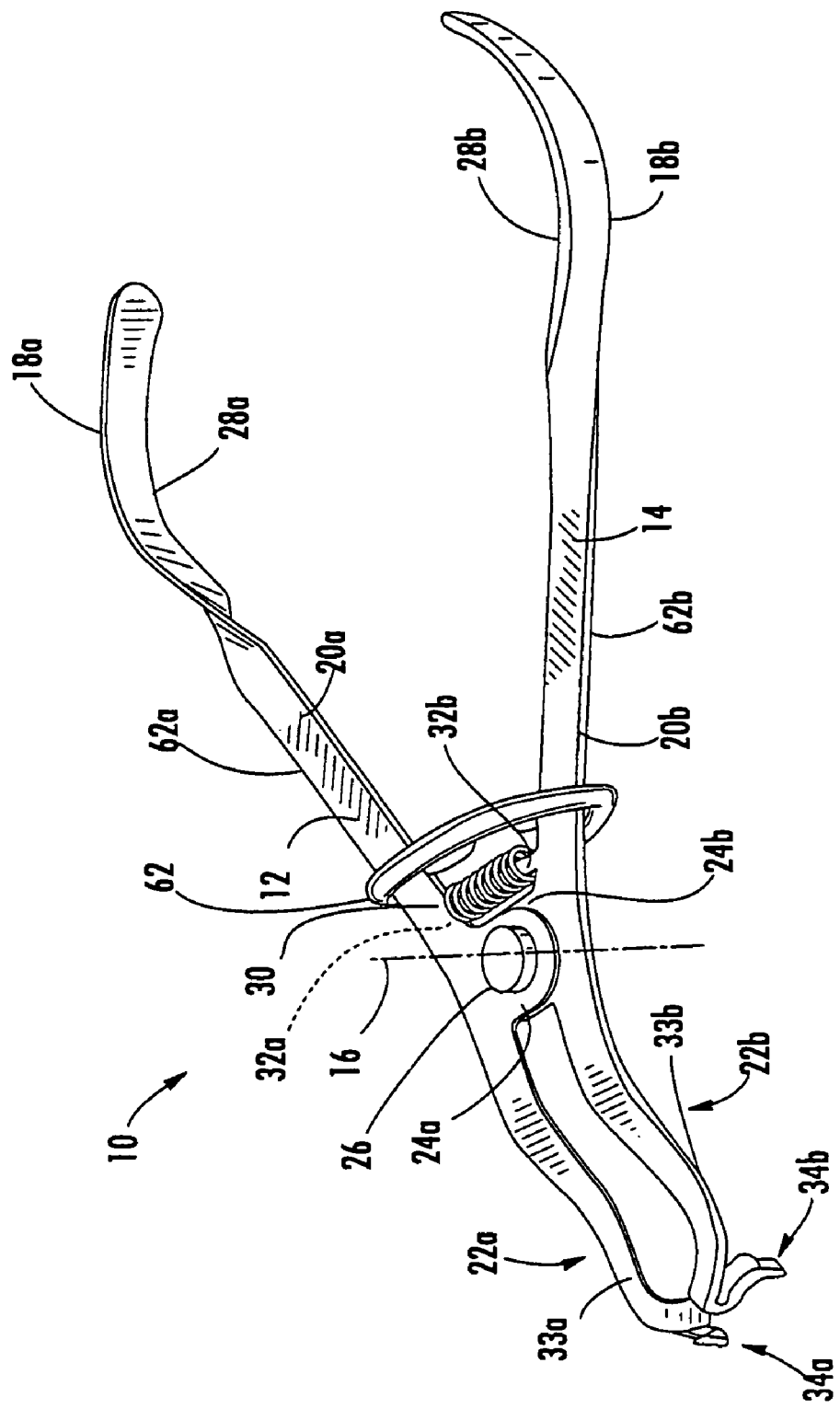
FIG. 1 is a perspective view of a dental instrument of the present invention.

Referring to FIG. 1, the numeral 10 generally designates a dental instrument of the present invention. As will be more fully described below, dental instrument 10 is configured to hold and capture a dental retaining ring and, further, to engage a rubber-dam clamp to permit placement of the rubber-dam clamp in a patient's mouth.

As best seen in FIG. 1, dental instrument 10 includes a pair of arms 12 and 14, which are pivotally coupled about a pivot axis 16. Each arm 12, 14 includes a proximal portion 18a, 18b, a medial portion 20a, 20b, and a distal portion 22a, 22b. Medial portions 20a, 20b include inwardly extending tabs or flanges 24a, 24b, which are connected by a pin 26, which is aligned with axis 16 to thereby pivotally couple arms 12 and 14 about their respective medial portions (20a, 20b). As will be more fully described below, distal portions 22a, 22b are adapted to engage both a rubber-dam clamp and, further, dental retaining rings.

In the illustrated embodiment, arms 12 and 14 are formed from plate members, such as stainless steel plate members that have a generally uniform cross-section from proximal portions 18a, 18b to medial portions 20a, 20b and which are rotated or twisted at the juncture between proximal portions 18a, 18b and medial portions 20a, 20b about the longitudinal axis of the respective plate members such that proximal portions 18a, 18b assume a generally orthogonal orientation with respect to medial portions 20a, 20b to thereby form handle portions 28a, 28b.

Arms 12 and 14 are biased such that handle portions 28a, 28b are urged outwardly or to separate while distal portions 22a, 22b are biased inwardly by a spring 30. In the illustrated embodiment, spring 30 comprises a coil spring that is mounted to inwardly projecting tabs or flanges 32a, 32b formed on medial portions 20a, 20b. In this manner, when the biasing force applied by spring 30 is unopposed, the distal portions 22a, 22b will be urged towards each other until they contact. However, it should be understood that spring 30 may comprise other types of springs.

Referring to FIGS. 2–5, distal portions 22a and 22b include first generally horizontal portions 33a, 33b (as viewed in FIG. 3) and prongs or prong portions 34a and 34b that depend downwardly from portions 33a and 33b, respectively. As will be more fully described, prongs 34a and 34b are configured or adapted to capture and firmly hold a dental retaining ring and, further, preferably configured to capture a dental retaining ring in two planes to eliminate the rocking associated with prior art forceps.

Figure 12:
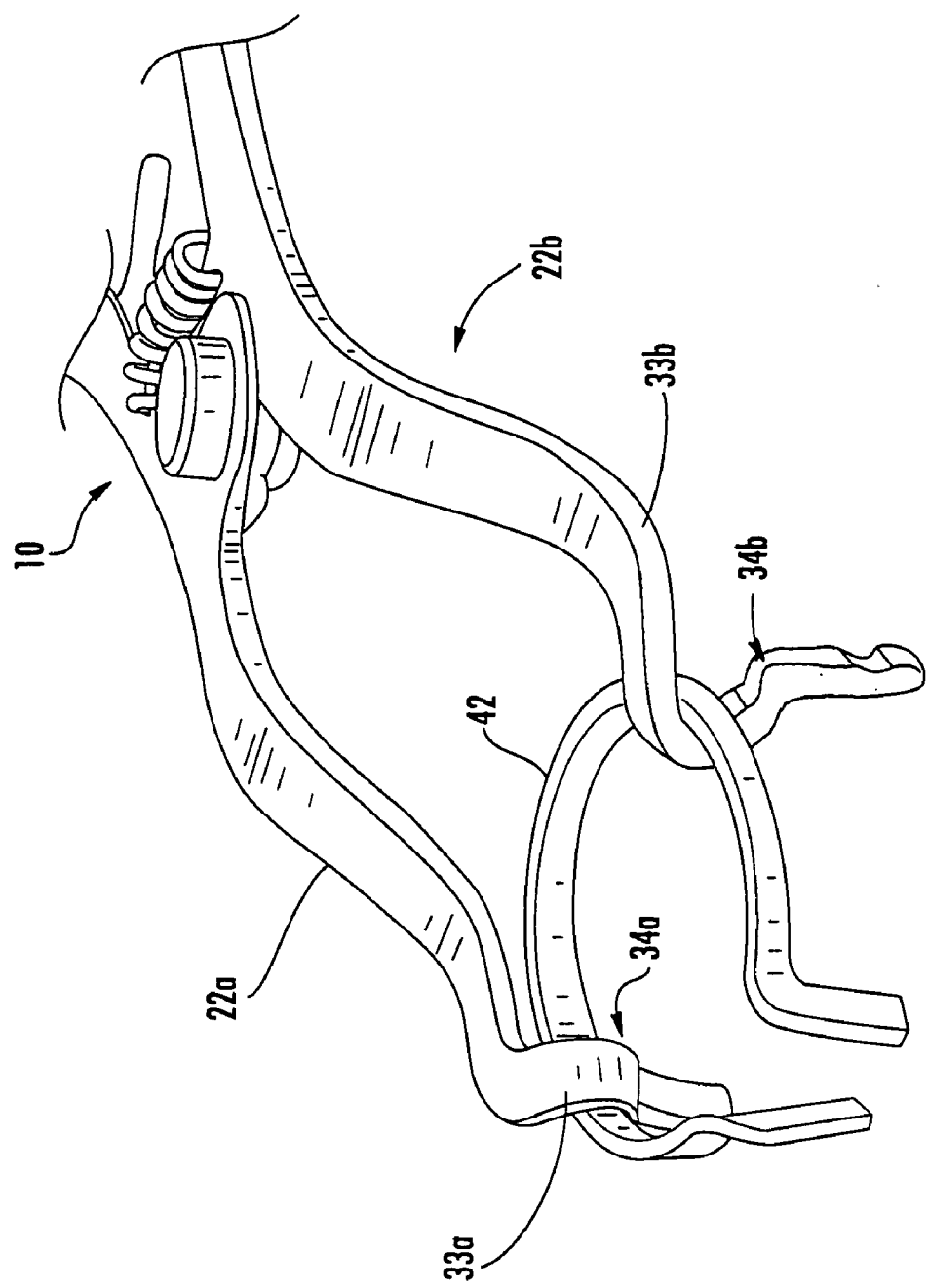
FIG. 12 is a similar view to FIG. 8 illustrating a dental instrument holding another embodiment of the dental retaining ring.

In the illustrated embodiment, as best seen in FIG. 3 the upper portions of prongs 34a and 34b comprise generally C-shaped portions 36a and 36b that form recesses or seats 38a and 38b for engaging and capturing a dental retaining ring therein, such as retaining ring 40 (FIG. 8) or retaining ring 42 (FIG. 12). While only two retaining rings are illustrated, it will be understood by those skilled in the art that instrument 10 may be used to similarly capture other retaining rings with different cross-sections and/or shapes. Extending downwardly from C-shaped portions 36a and 36b are tines 44a and 44b (FIG. 3), which form the lower portions of prongs 34a and 34b. Tines 44a and 44b are adapted to engage a rubber-dam clamp 46 (FIG. 6), as will be more fully described below.

As best seen in FIGS. 2, 4, and 5, tines 44a, 44b include upper portions 48a, 50a and lower portions 48b, 50b. Upper portions 48a, 50a extend downwardly from the ends of seats 38a, 38b. Lower portions 48b and 50b have a smaller width dimension than their respective upper portions 48a and 50a and, further, are sized so that they can be inserted into the respective rubber-dam clamp openings 52a and 52b. In the illustrated embodiment, upper portions 48a, 50a are aligned with lower portions 48b and 50b so that lower portions 48b, 50b are also aligned with the ends of seats 38a, 38b. Furthermore, tines 44a and 44b preferably include elongate grooves 54a and 54b between the upper and lower portions 48a, 50a and 48b, 50b so that when lower portions 48b and 50b are inserted into the apertures 52a and 52b of rubber dam clamp 46, and the pressure is applied to dental instrument 10, clamp 46 will be seated in grooves 54a and 54b. In addition, clamp 46 will rest against the respective lower surfaces 58a and 58b of upper portions 48a and 50a to steady the clamp and, further, limit penetration of tines 44a and 44b into clamp 46. In this manner, clamp 46 is firmly engaged by tines 44a and 44b when handle portions 28a and 28b of instrument 10 are squeezed together and distal portions 22a and 22b are separated, as would be understood by those skilled in the art.

As previously noted, spring 30 applies a biasing force to arms 12 and 14 to urge arms 12 and 14 to pivot about pivot axis 16 such that distal portions 22a and 22b are urged towards each other and, further when unopposed, urged towards each other such that respective apexes 60a and 60b of C-shaped portions 36a and 36b make contact. As best seen in FIG. 3, when C-shaped portions 36a and 36b are urged towards each other and contact each other, tines 44a and 44b are separated and, further, preferably separated a distance generally equal to the spacing between openings 52a and 52b of clamp 46. In this manner, instrument 10 may be positioned to engage clamp 46 without compressing handle portions 28a and 28b. As will be described in reference to another embodiment, the spacing between the tines may be adjusted.

To facilitate the positioning of distal portions 22a and 22b, instrument 10 further includes a strap 62, which straddles arms 12 and 14. Outer edges 62*a* and 62*b* of arms 12 and 14 include a plurality of serrations or notches that are engaged by the inner edges of the respective sides of strap 62 to thereby fix the orientation of arms 12 and 14 until the strap is released from engagement with the respective serrations or grooves. In this manner, the relative positions of prongs 34*a* and 34*b* may be releasably fixed to reduce the strain on the hand of the operator of instrument 10, which is particularly suitable when instrument 10 is used to engage a retaining ring, described below.

Figure 8:
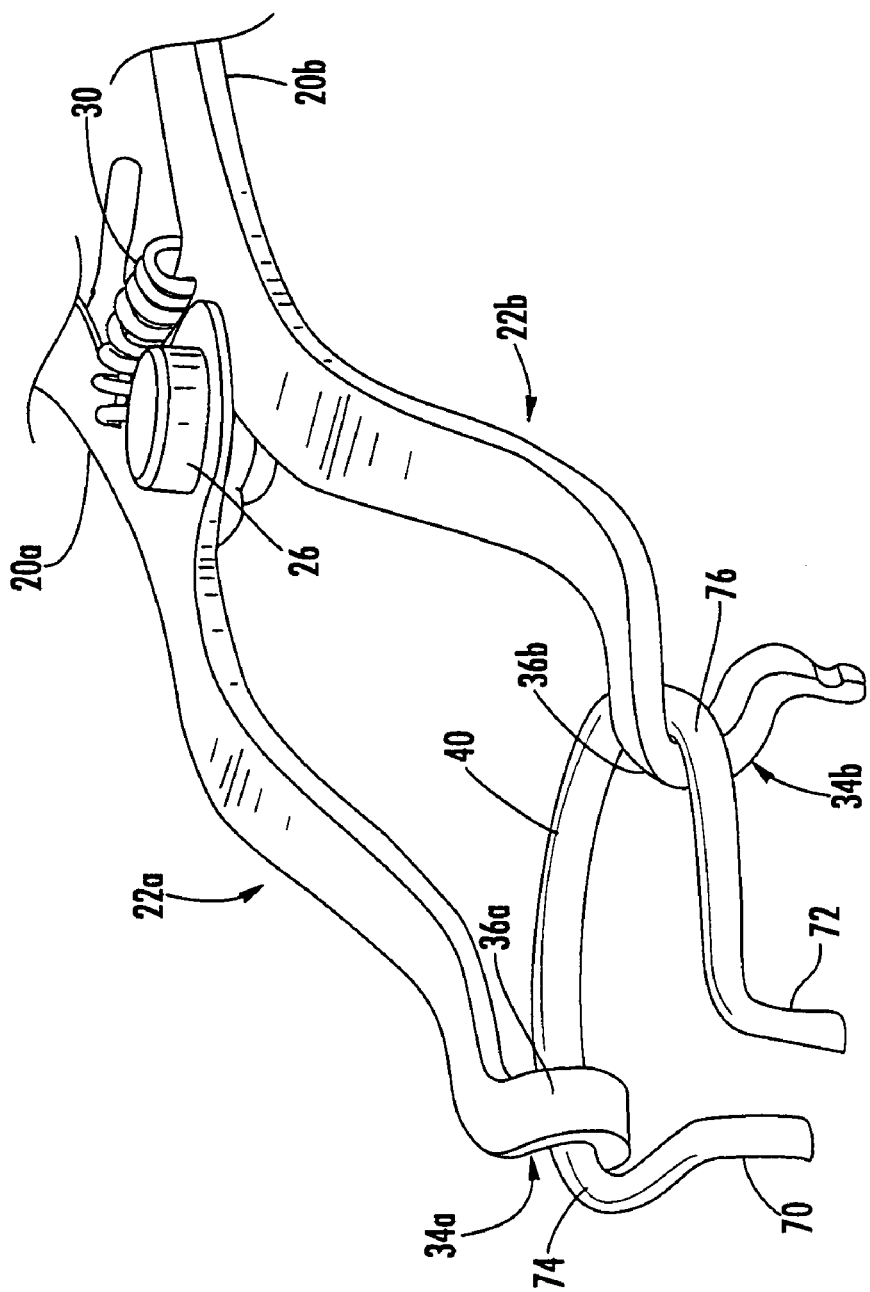
FIG. 8 is an enlarged fragmentary perspective view of the dental instrument of FIG. 1 holding a dental retaining ring.
Figure 9:
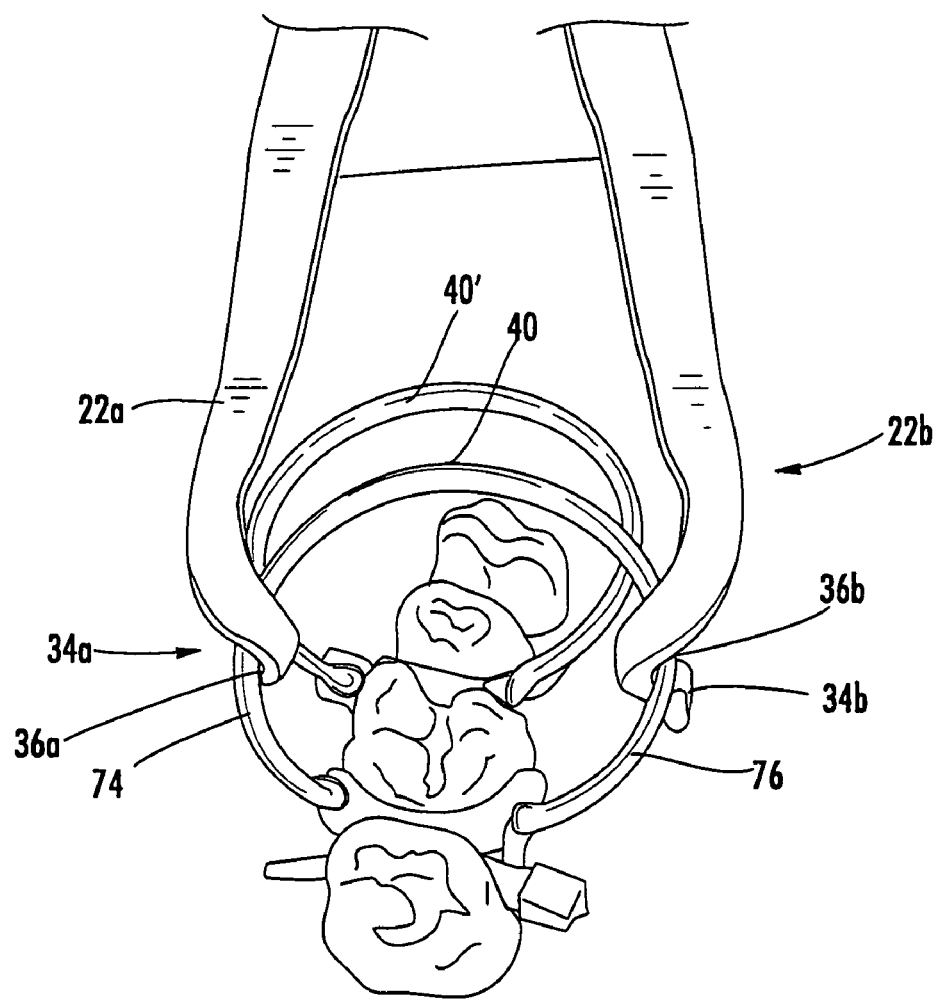
FIG. 9 is a top perspective view of the dental instrument of FIGS. 1–8 positioning the dental retaining ring between adjacent teeth and, further, over a previously placed dental retaining ring.

As previously noted, instrument 10 is adapted to hold and, further, separate dental retaining rings of a sectional matrix system. Referring to FIG. 8, retaining ring 40 comprises an open-ended ring with downwardly depending tines 70, 72 that require separation to place the ring between adjacent teeth of a patient, such as illustrated in FIG. 9. Retaining rings are commonly used in sectional matrix systems and are used to separate teeth and, further, to hold a tooth reconstruction element, such as a contour band (typically a thin band, which is usually made of stainless steel or the like), in place around a tooth when a cavity in a tooth is to be filled.

When a tooth includes a decayed portion, the decayed portion is excavated and then filled. When the decayed portion is located near the tooth's interproximal area, the tooth structure is usually insufficient to provide support for the filling material during the filling process. In order to retain the filling material in the cavity while it hardens, the tooth reconstruction element is positioned about the tooth and secured tightly about the tooth such that the element forms an outer shell or matrix. In this manner, the reconstruction element allows the filling material to fill the excavated portion of the tooth and harden into its correct shape. However, in order to accommodate the thickness of the reconstruction element and the shrinkage of the filling material, typically a composite resin, as the filling material cures, the adjacent teeth must be separated. In order to properly place the retaining ring between the teeth, the tines are separated, which causes the ring to generate an inward spring force, which, thus, separates the teeth. To assure proper placement of the retaining ring between the teeth, it is preferable that the retaining ring remain stable during placement.

Figure 13:
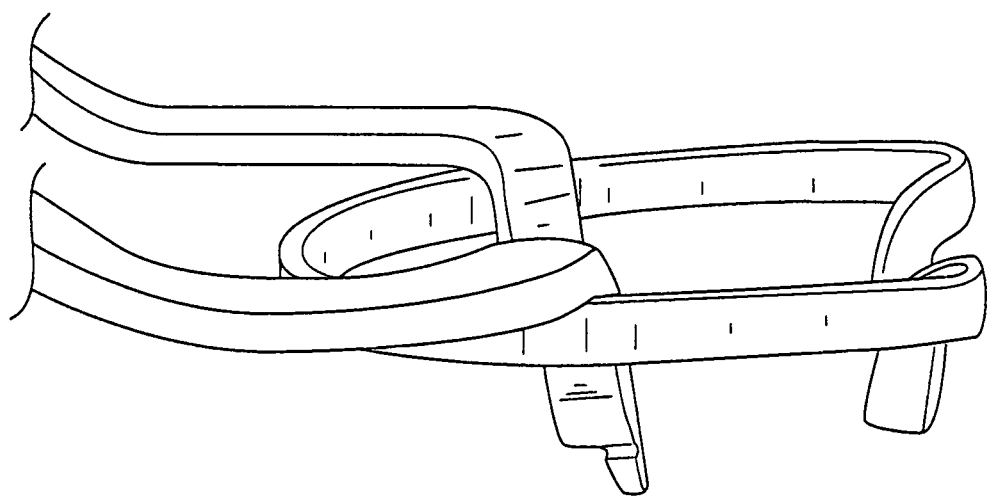
FIG. 13 is a side elevation view of the dental instrument of the present invention holding the second embodiment of the retaining ring.

As noted previously, prongs 34*a* and 34*b* of instrument 10 are adapted to capture a retaining ring and, preferably, capture a retaining ring in two planes. To engage the retaining ring, the distal portions 22*a* and 22*b* of instrument 10 are aligned over the ring with prongs 34*a* and 34*b* located between the arms 74 and 76 of retaining ring 40. Further, C-shaped portions 36*a* and 36*b* are aligned with arms 74 and 76 so that when handle portions 28*a* and 28*b* are squeezed and compressed to separate distal portions 22*a* and 22*b*, arms 74 and 76 of retaining ring 40 will be engaged by and seated in C-shaped portions 36*a* and 36*b* so that arms 74 and 76 of ring 40 will be separated and tines 70 and 72 of ring 40 may be properly placed between the adjacent teeth, as shown in FIG. 9. Furthermore, the C-shaped portions 36*a* and 36*b* provide at least a multiple point contact between each prong and each arm 74, 76 of ring 40 and, further, in some cases, depending on the cross-section of the ring, provide a surface contact for each arm 74, 76. For example, the inner surfaces of C-shaped portions 36*a* and 36*b* may be slightly angled or non-parallel with respect to each other to better follow the contour of a matrix ring, which is typically grabbed between the rings tines and the midpoint's of the ring where the opposed inner surfaces of the ring are not mirror images, and instead are non-parallel and angled with respect to each other. Further, with some rings, the ring will be captured between lower planar surfaces of first portions 33*a*, 33*b* and seats 38*a* 38*b*, as shown in FIGS. 8 and 13. In this manner, the ring arms 74, 76 are captured by prongs 34*a* and 34*b* in at least two planes, which eliminates the instability and, hence, the rocking of the retaining ring associated with rubber dam clamp forceps.

Figure 30:
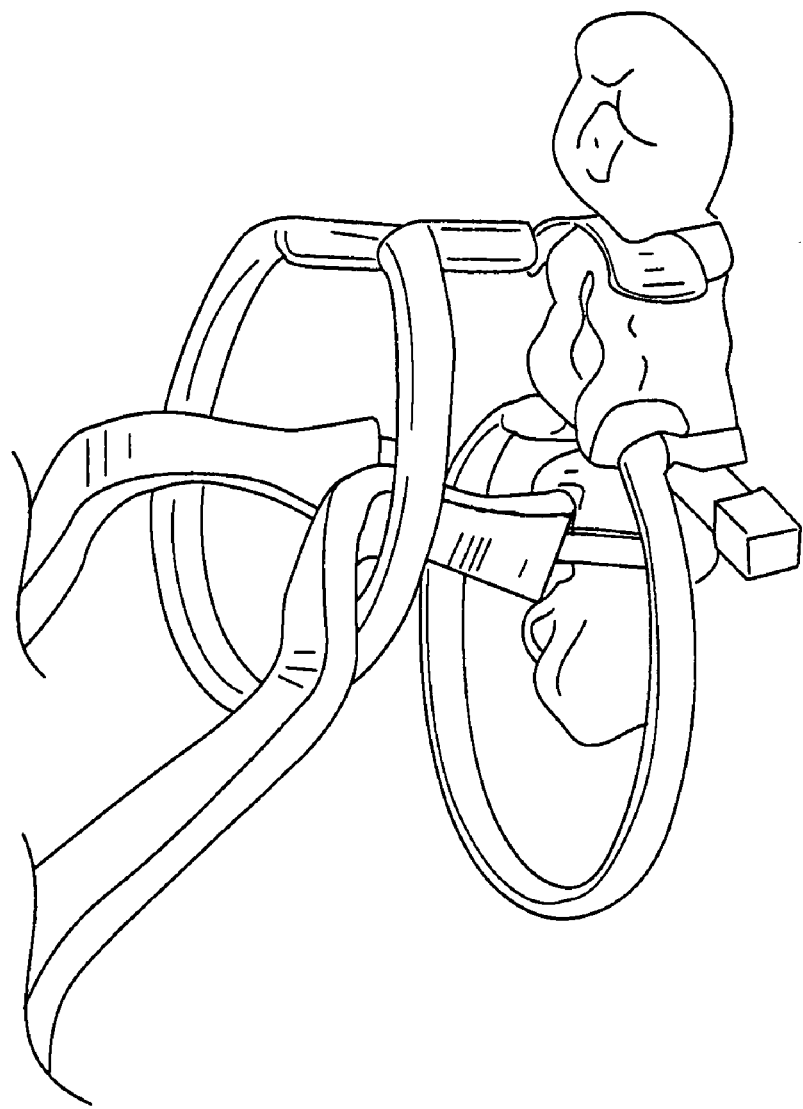
FIG. 30 is a side perspective view of the prior art rubber-dam clamp of FIGS. 27–29 illustrating the interference between the tines of the forceps and a dental retaining ring.

As will be understood by those skilled in the art, it is common for multiple retaining rings to be positioned in a patient's mouth. For example, two rings are often used where restoration is required on both sides (both interproximal areas) of a tooth, such as shown in FIG. 9, or on adjacent teeth. In this scenario, it is particularly difficult to use a conventional rubber-dam forceps to place the rings since the tines of the prior art rubber-dam clamp forceps often interfere with the placement of the later placed ring, such as shown in FIG. 30.

Figure 10:
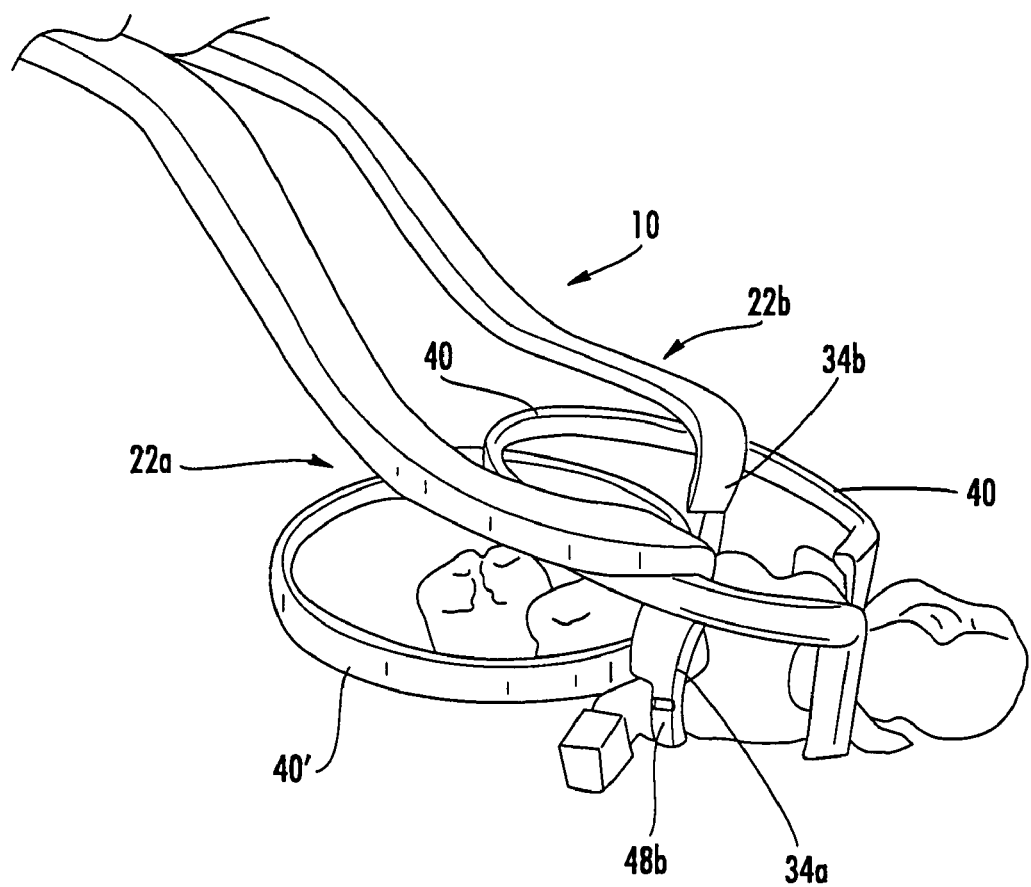
FIG. 10 is a side elevation view of the illustration of FIG. 10 illustrating the placement of a dental ring between adjacent teeth.
Figure 11:
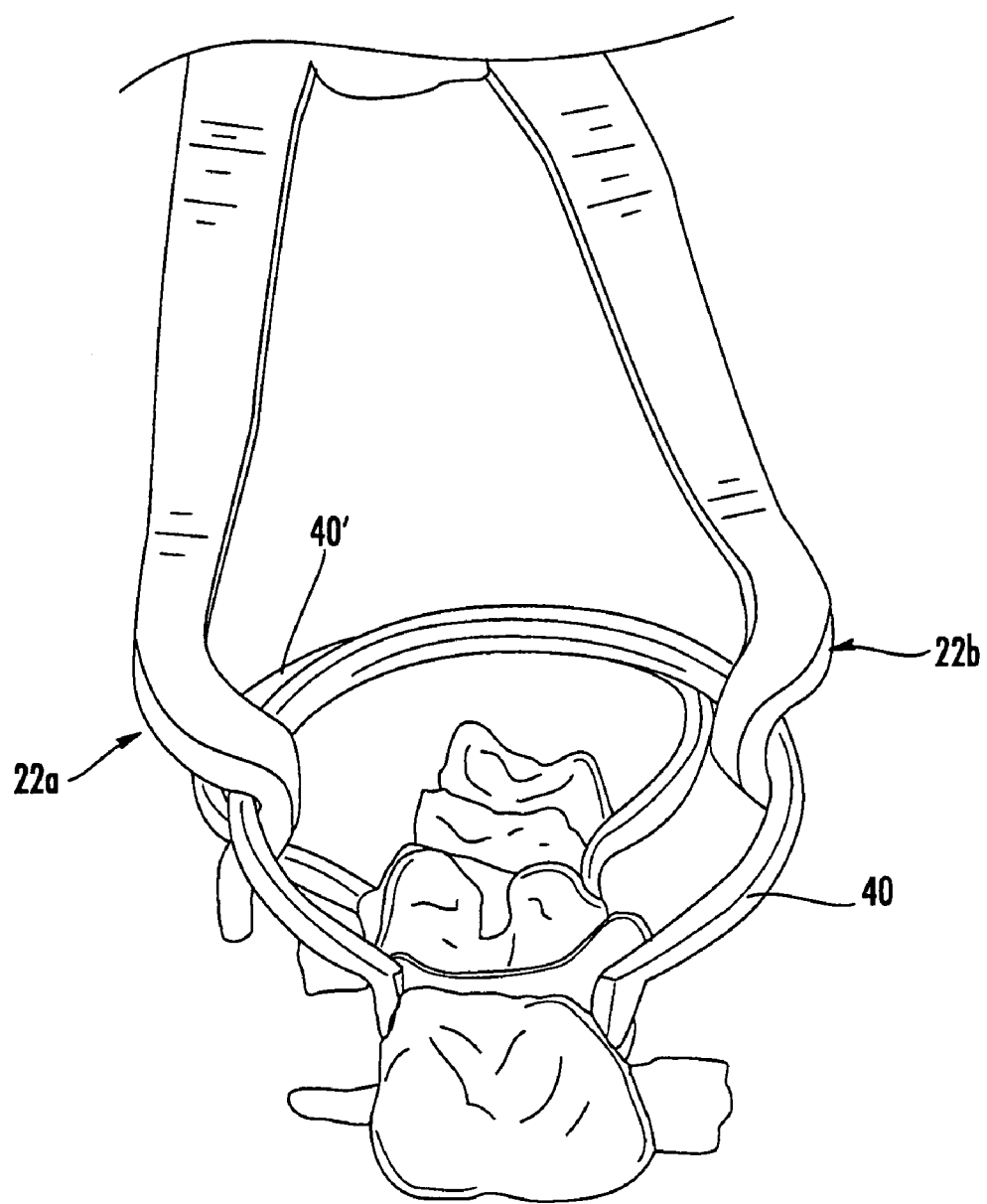
FIG. 11 is a similar view to FIGS. 9–10 illustrating the clearance between the dental retaining ring and the prongs of the dental instrument.

As best seen in FIGS. 9–11, when placing a second retaining ring, prongs 34*a* and 34*b* of instrument 10 are configured to minimize interference with the previously placed ring 40'. As best seen in FIG. 10, the overall height of prongs 34*a* and 34*b* are significantly reduced compared to the prior art rubber-dam forceps and, further, provide multiple contact points with the respective arms 74 and 76 of ring 40 to thereby capture the ring and firmly hold the retaining ring which limits rocking or turning of the retaining ring in instrument 10 to provide increased control over the placement of retaining ring 40 in a patient's mouth.

In addition, referring to FIGS. 2–5, prongs 34*a* and 34*b* have length in a range of about 6 to 11 mm and, more preferably, in a range of about 6.5 to 9.5 mm to thereby minimize the contact of the prongs with the teeth or gums of the patient. The length of the lower portions of the respective tines are in a range of 1 to 2 mm and, more preferably, in a range of 1.3 to 1.7 mm and, most preferably, approximately 1.5 mm. Furthermore, by moving or shifting the lower ends 48*b*, 50*b* of tines 44*a*, 44*b* forward relative to the longitudinal central axis of the prongs, an interference between a previously placed ring 40' (FIGS. 9–11) will be minimized. In addition, the potential for entanglement with the rubber-dam itself will also be minimized.

Referring again to FIG. 5, prongs 34*a* and 34*b* are preferably angled with respect to first portions 33*a* angled at an angle A in a range of about 76° to 84° and, more typically, in a range of about 74° to 82° and, most typically, about 80°. In this manner, prongs 34*a* and 34*b* are angled forward relative to the plane in which first portions 33*a* and 33*b* in a range of 96° to 104°, more typically, in a range of about 98° to 102° and, most typically, about 100°. Furthermore, because first portions 33*a* are generally parallel and offset from the plane in which proximal portions 18*a* and 18*b* and medial portions 20*a* and 20*b* pivot, prongs 34*a* and 34*b* are similarly angled with respect to the plane in which the medial portions and proximate portions pivot. Furthermore, by angling prongs 34*a* and 34*b* forward, prongs 34*a* and 34*b* fall outside the previously positioned ring. Hence, the interference between the prongs and a previously placed ring is reduced.

Figure 14:
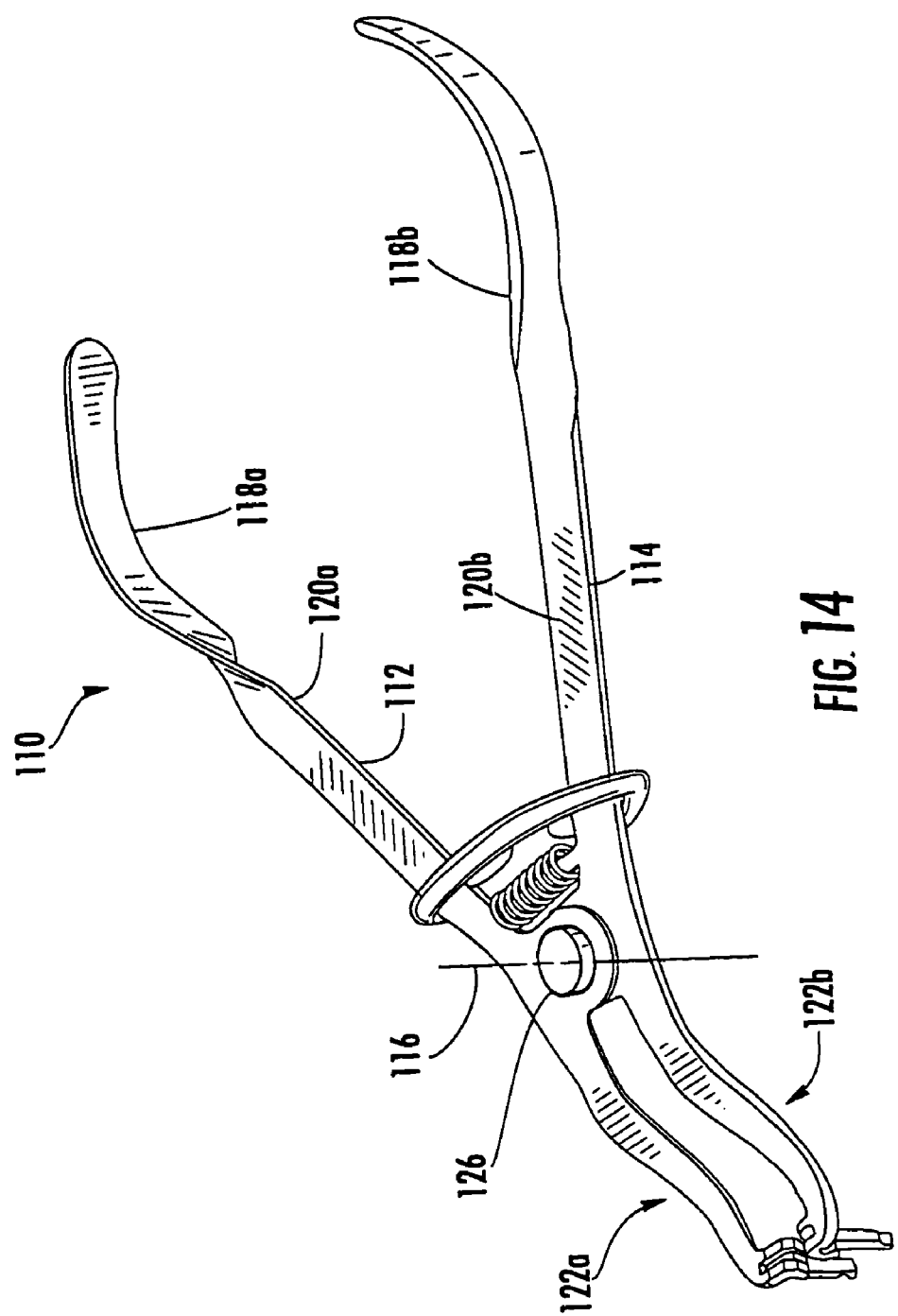
FIG. 14 is a perspective view of another embodiment of the dental instrument of the present invention.

Referring to FIG. 14, the numeral 110 generally designates another embodiment of the dental instrument of the present invention. Dental instrument 110 is of similar construction to dental instrument 10 and includes a pair of arms 112 and 114, which are pivotally coupled about an axis 116 by a pin 126. Each arm 112 and 114 includes a proximal portion 118*a*, 118*b*, a medial portion 120*a*, 120*b*, and a distal portion 122*a*, 122*b*, respectively. For further details of proximal and medial portions 118*a*, 118*b*, 120*a*, 120*b* reference is made to the first embodiment.

Figure 15:
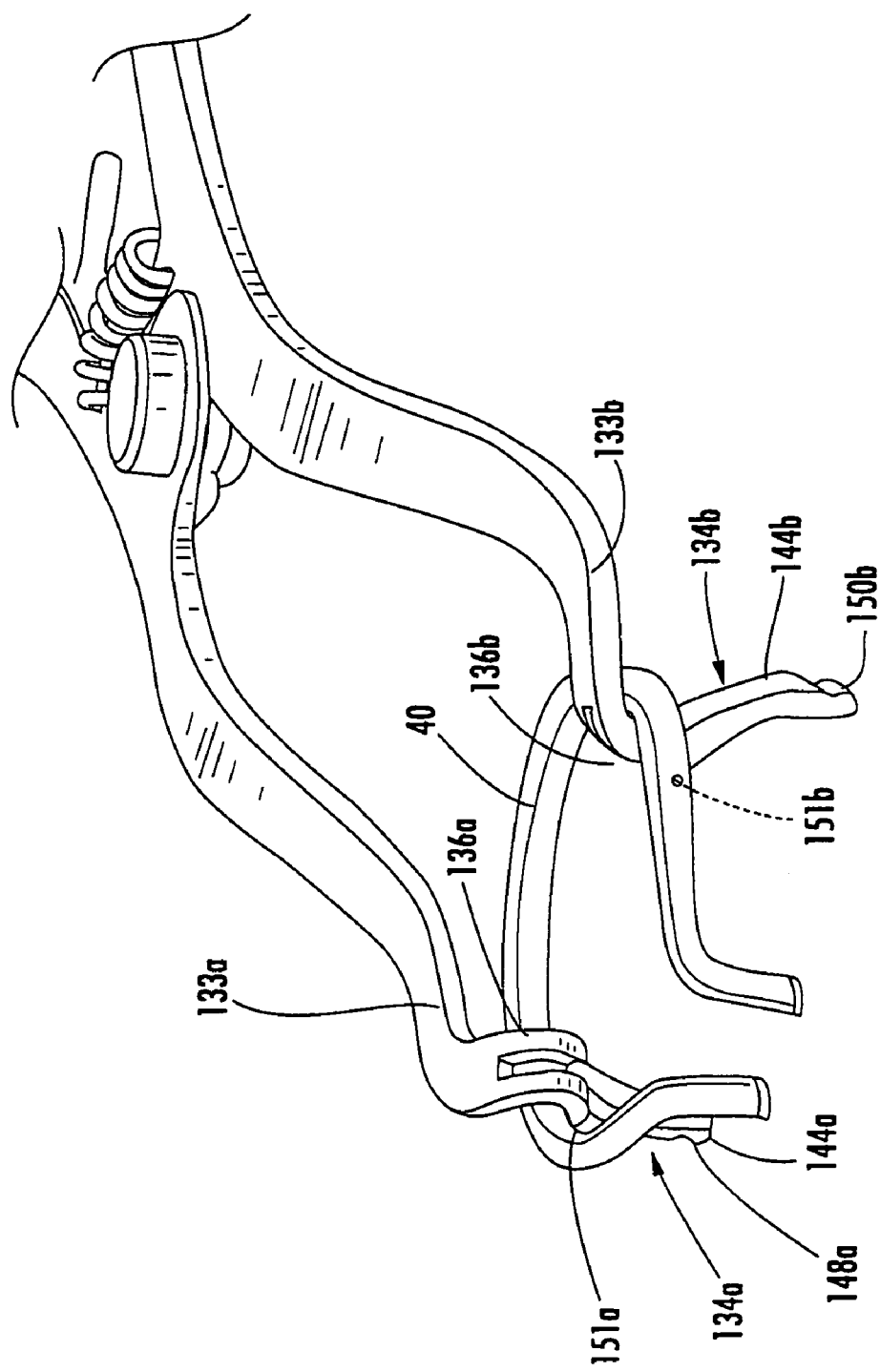
FIG. 15 is an enlarged fragmentary perspective view of the dental instrument of FIG. 14 holding the first embodiment of the dental retaining ring of the present invention.

In the second embodiment, distal portions 122a and 122b include prongs 134a and 134b that depend from first portions 133a and 133b in a similar manner to the previous embodiment. However, in the present embodiment, prongs 134a and 134b include pivotal tines 144a and 144b, which are pivotally mounted to C-shaped portions 136a and 136b so that tines 144a and 144b may be rotated or pivoted between a stored position where they do not project below C-shaped portions to eliminate any potential interference with the placement of the ring 40 and an extended position (such as shown in FIG. 15) where lower or distal ends 148a and 150b are positioned for engaging a rubber-dam clamp. For example, tines 144a and 144b may be pivotally mounted to C-shaped portions 136a and 136b by pins 151a and 151b and, further, incorporate a detent mechanism so that the tines are held in their respective positions unless acted upon by a force sufficient to release the detent mechanism.

Figure 16:
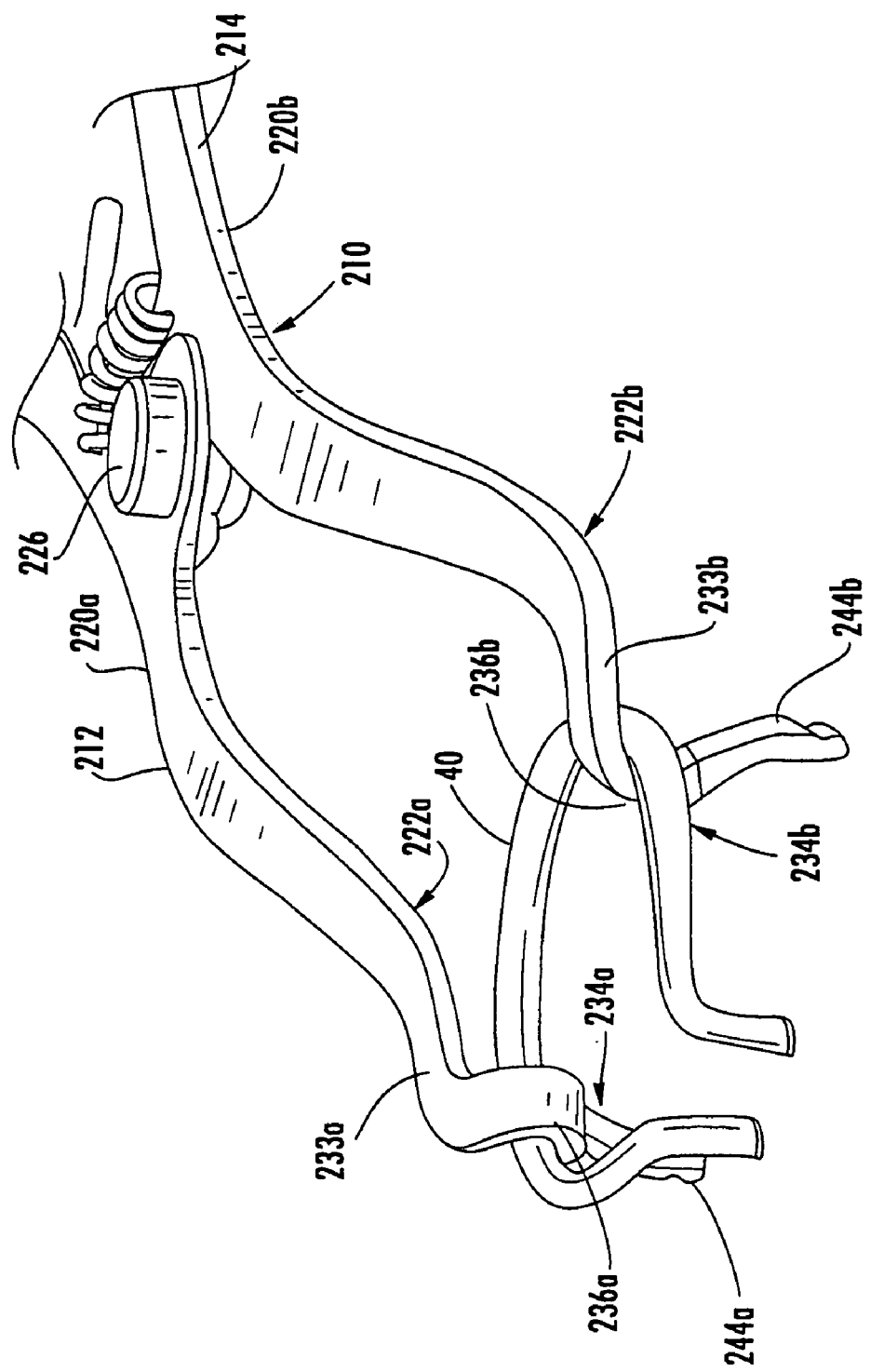
FIG. 16 is an enlarged fragmentary perspective view of a third embodiment of the dental instrument of the present invention holding a dental retaining ring.
Figure 17:
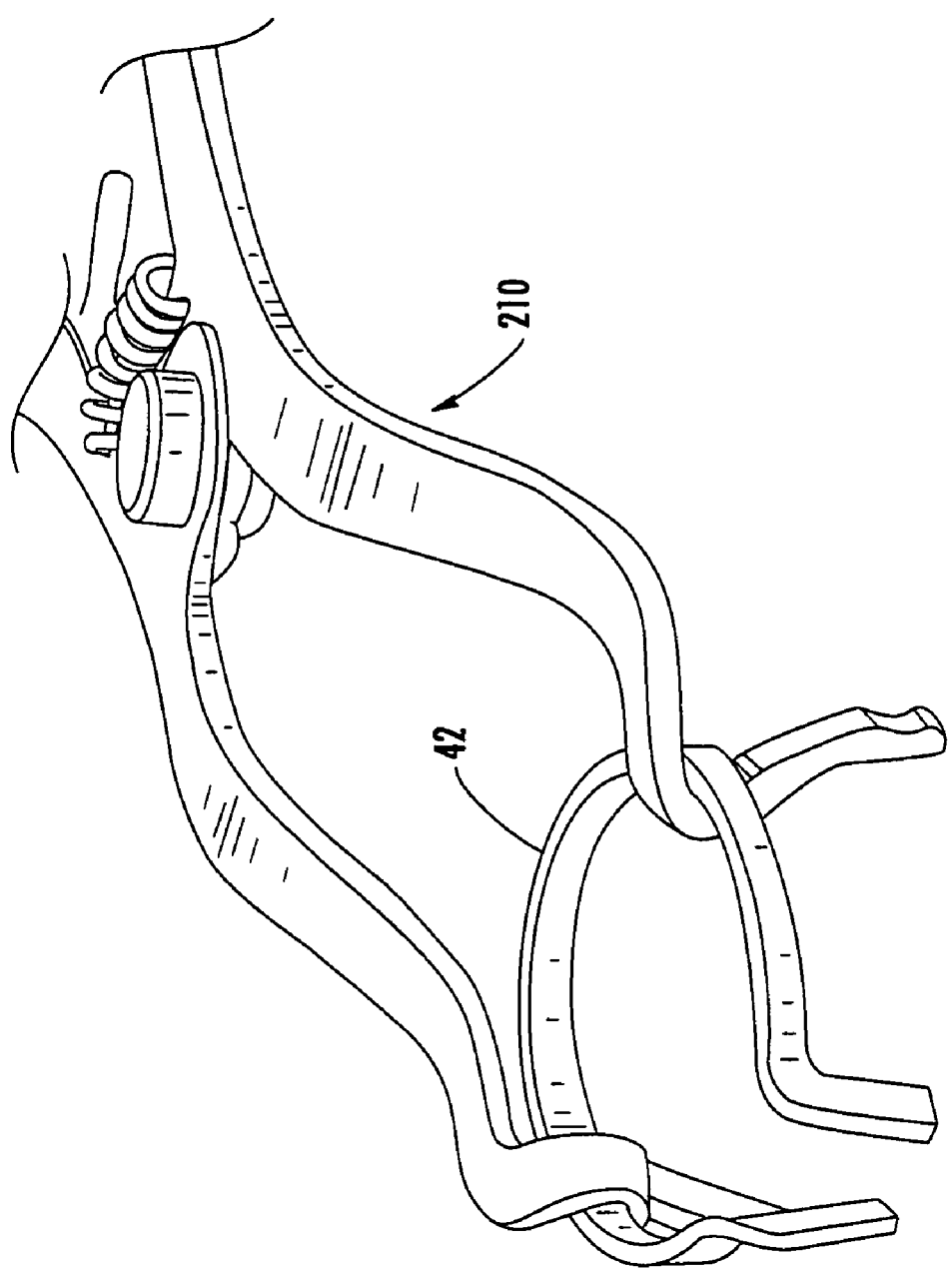
FIG. 17 is a similar view to FIG. 16 illustrating the dental instrument of FIG. 16 holding the second embodiment of the dental retaining ring.

Referring to FIG. 16, the numeral 210 designates yet another embodiment of the dental instrument of the present invention. Dental instrument 210 is of similar construction to the previous embodiments and includes a pair of arms 212 and 214, which are pivotally connect at their respective medial portions 220a and 220b by a pin 226. Distal end portions 222a and 222b include first portions 233a and 233b, which are generally horizontal, and prongs 234a and 234b that depend from first portions 233a and 233b similar to the previous embodiments.

In the illustrated embodiment, prongs 234a and 234b include a upper C-shaped portion 236a and 236b and tines 244a and 244b that depend from and, further, are releasably coupled to C-shaped portions 236a and 236b. In this manner, similar to the previous embodiment, tines portions 244a and 244b may be longer than the first embodiment but may be removed to avoid interference with placement of rings 40 or 40' and, further, to avoid entanglement with the rubber-dam. Instrument 210 may be used for rings with circular or oval cross-sections such as ring 40, or rings with rectangular cross-sections, such as ring 42, similar to the previous embodiments.

Referring to FIGS. 18–26, the dental instrument of the present invention may incorporate distal portions 322a and 322b, which are configured to provide more closely spaced tines 344a and 344b. Distal portions 322a and 322b include first portions 333a and 333b and prongs 334a and 334b, which depend from first portions 333a and 333b. The upper portions of prongs 334a, 334b comprise C-shaped portions 336a and 336b. Prongs 334a and 334b includes tines 344a and 344b, respectively, which depend from C-shaped portions 336a and 336b. Similar to the previous embodiments, tines 334a and 334b are adapted to engage a rubber-dam clamp so that the rubber-dam clamp can be positioned in the patient's mouth.

Figure 19:
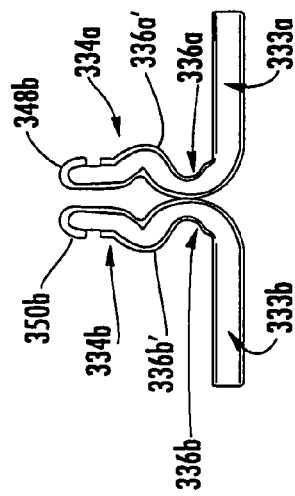
FIG. 19 is an inverted elevation view of the distal portions of the dental instrument of FIG. 18.
Figure 21:
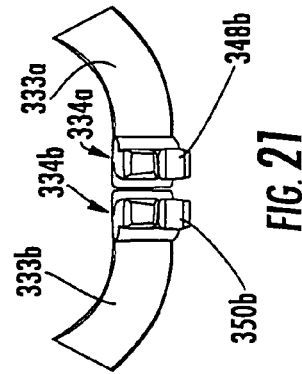
FIG. 21 is a bottom plan view of the distal portions of the dental instrument of FIGS. 18–20.
Figure 18:
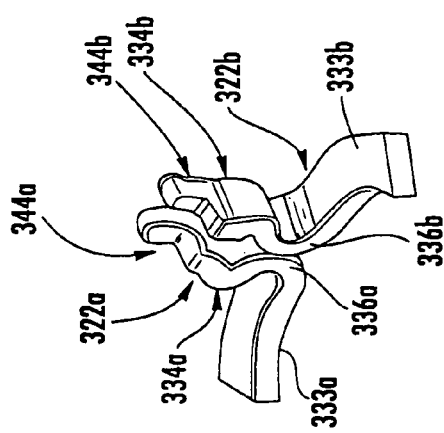
FIG. 18 is an inverted perspective view of the distal portions of another embodiment of the dental instrument of the present invention.
Figure 20:
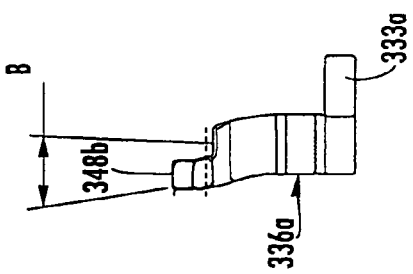
FIG. 20 is an inverted side view of the distal portions of the dental instrument of FIGS. 18–19.
Figure 22:
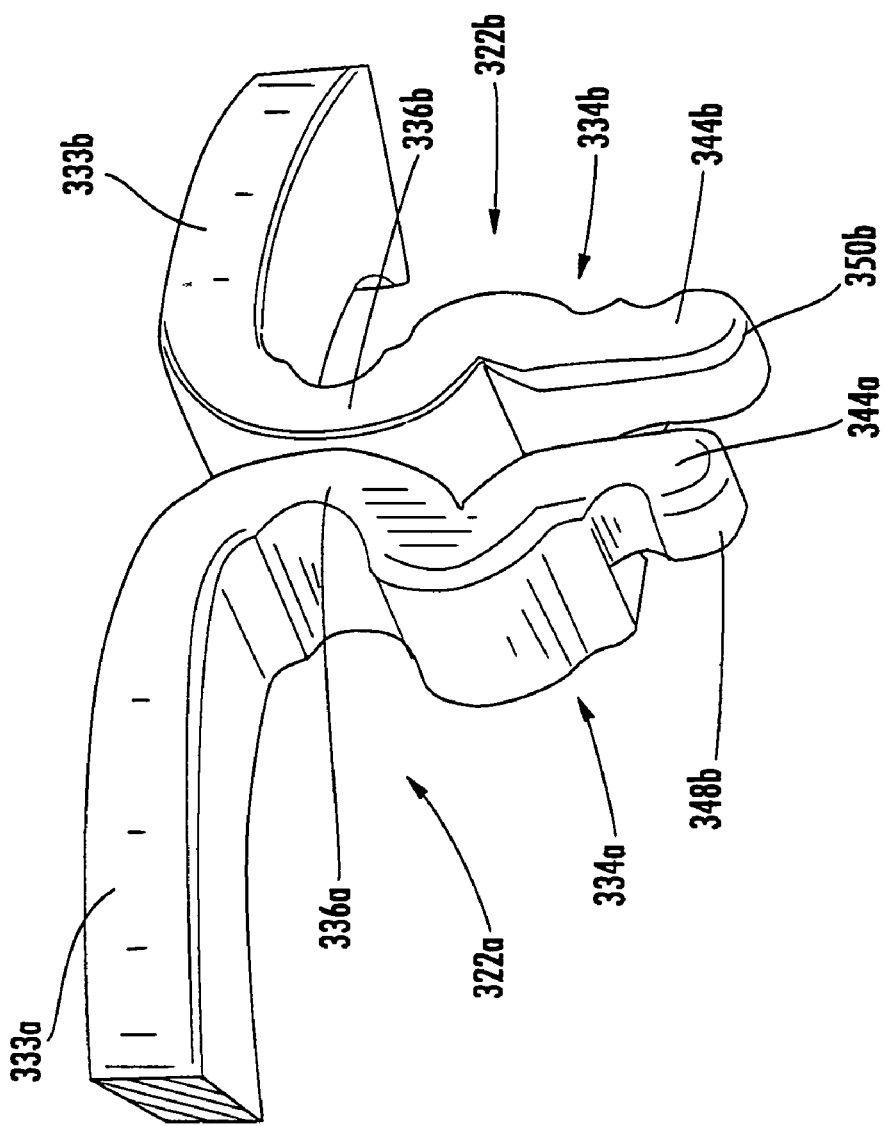
FIG. 22 is a front perspective view of the distal portions of the dental instrument of FIGS. 18–21.
Figure 23:
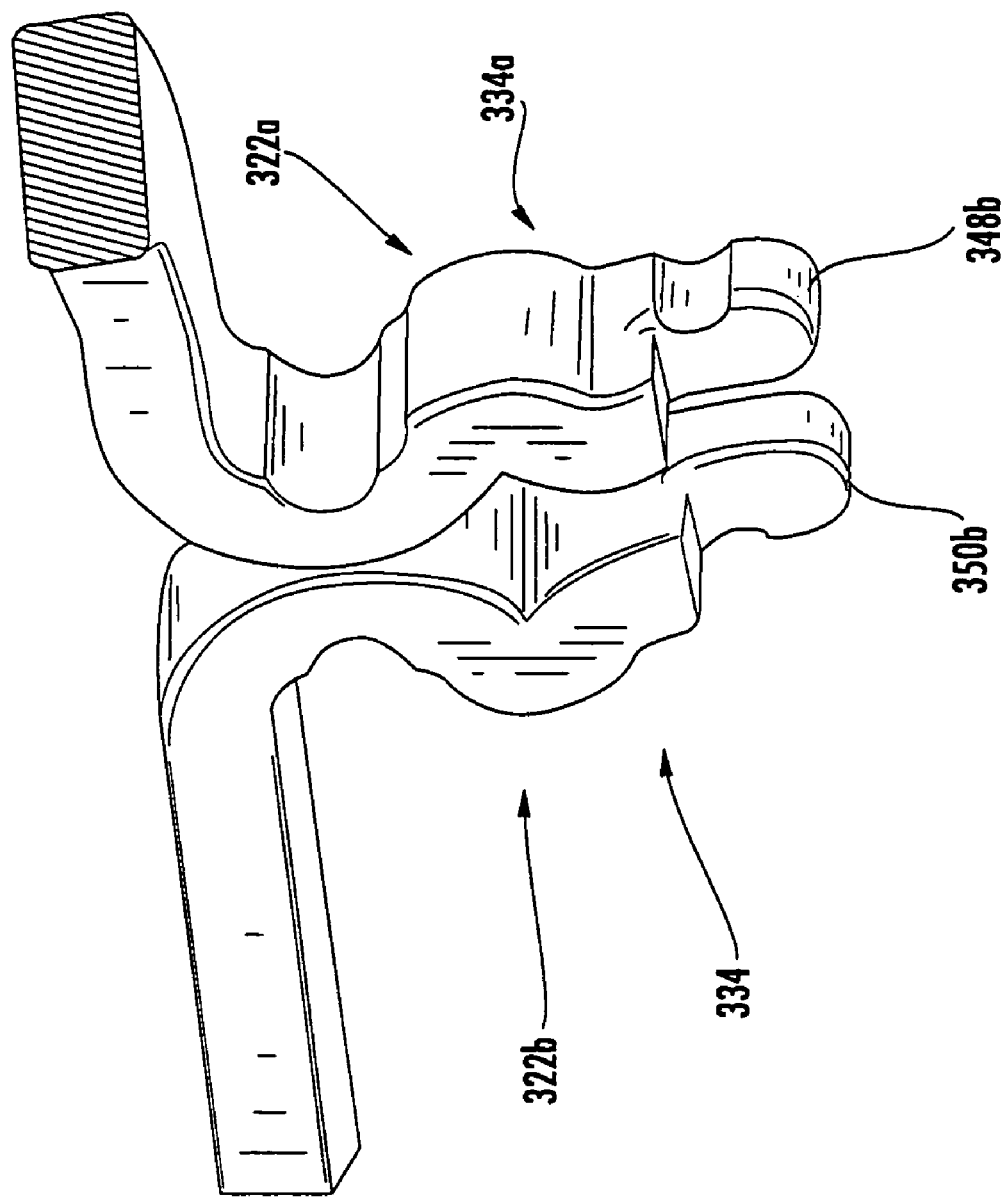
FIG. 23 is a rear perspective view of the distal portions of FIG. 22.
Figure 24:
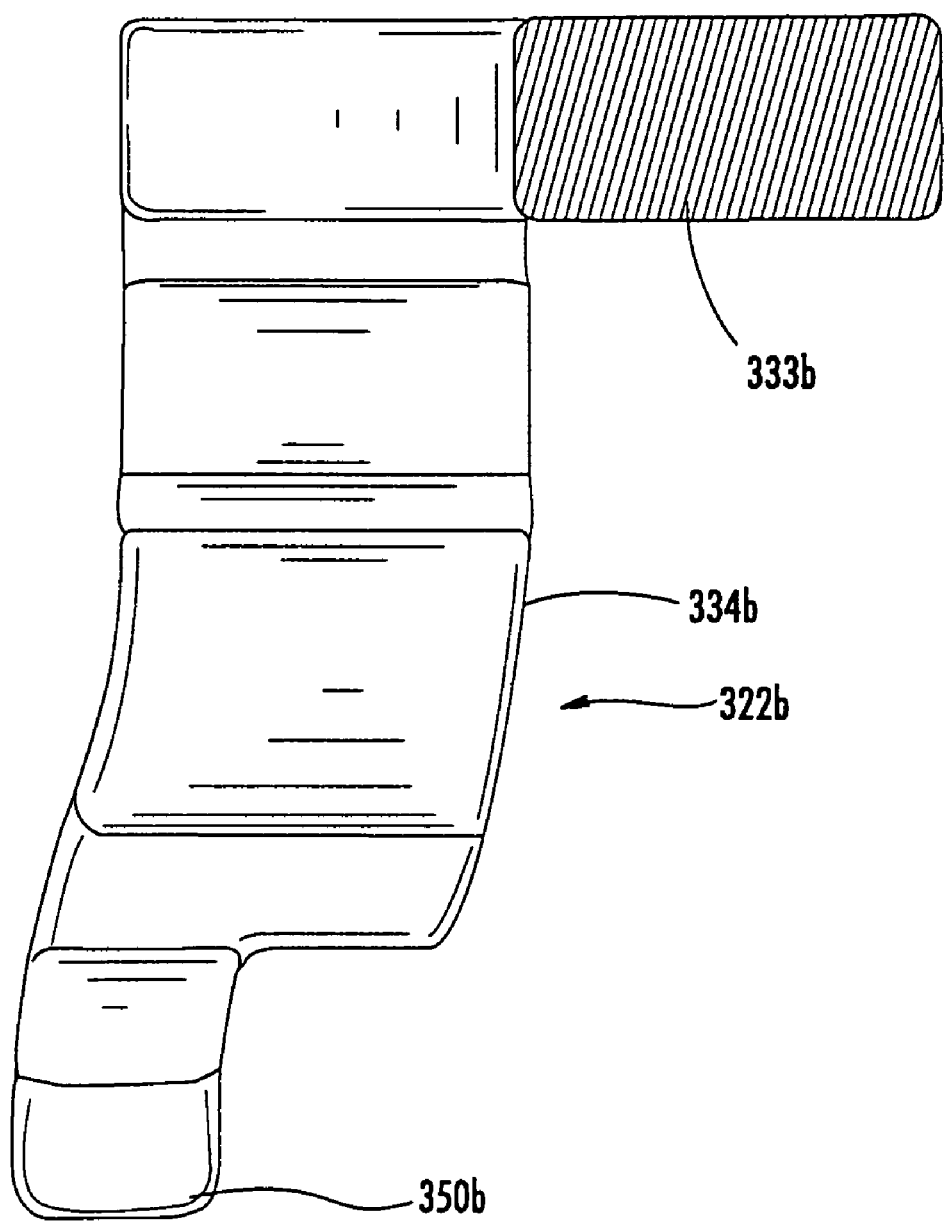
FIG. 24 is a side elevation view of the distal portions of FIGS. 22–23.
Figure 25:
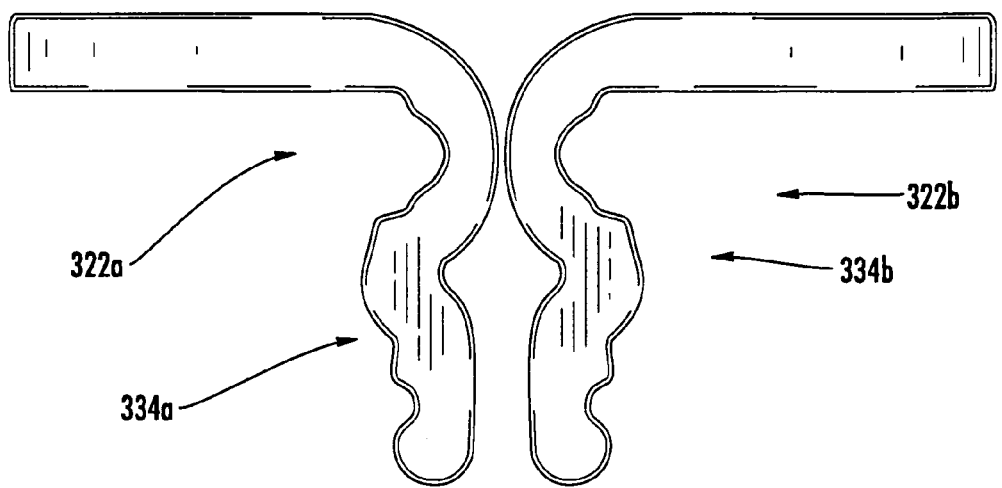
FIG. 25 is a front elevation view of the distal portions of FIG. 23.
Figure 26:
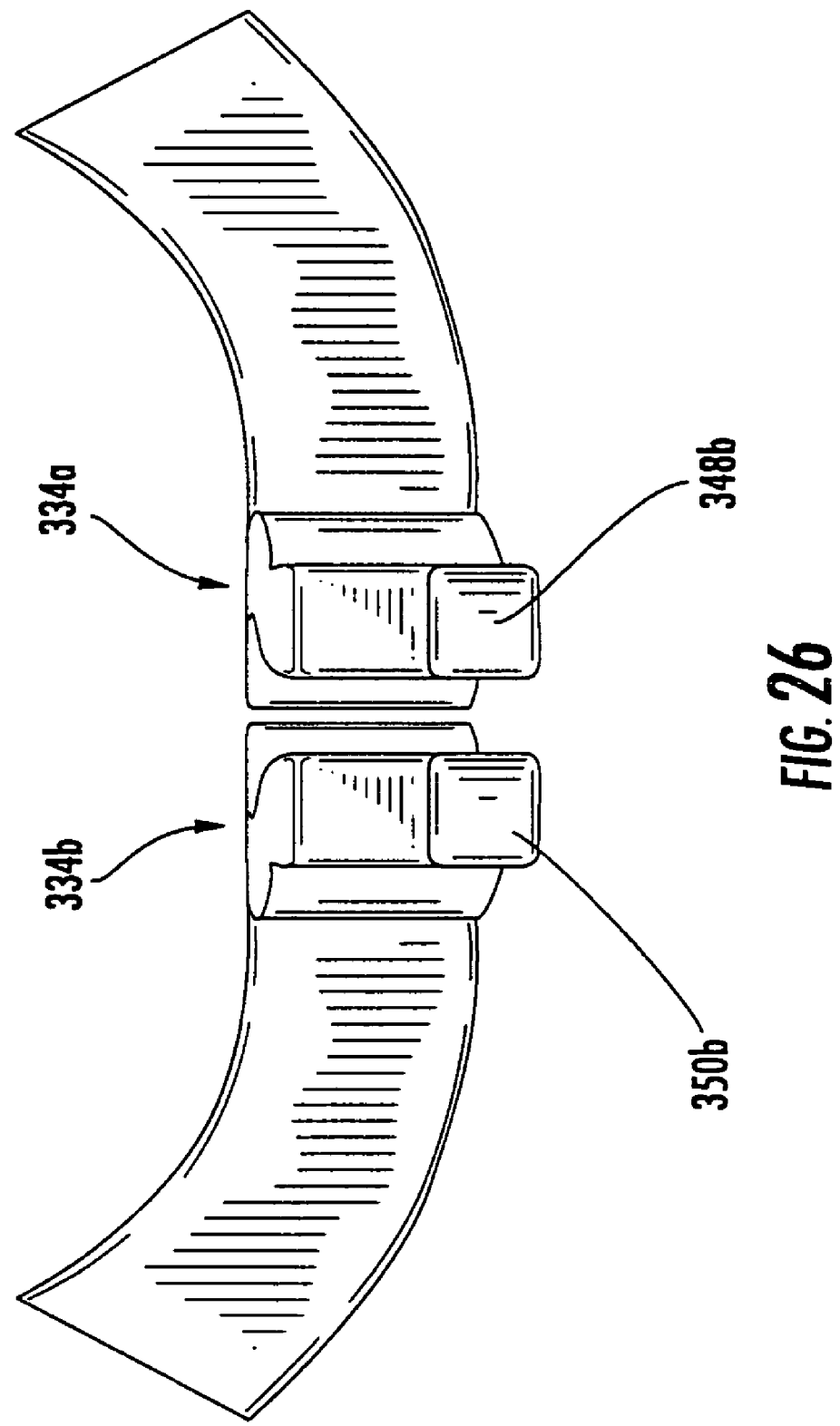
FIG. 26 is a bottom plan view of the distal portions of FIGS. 22–25.
Figure 27:
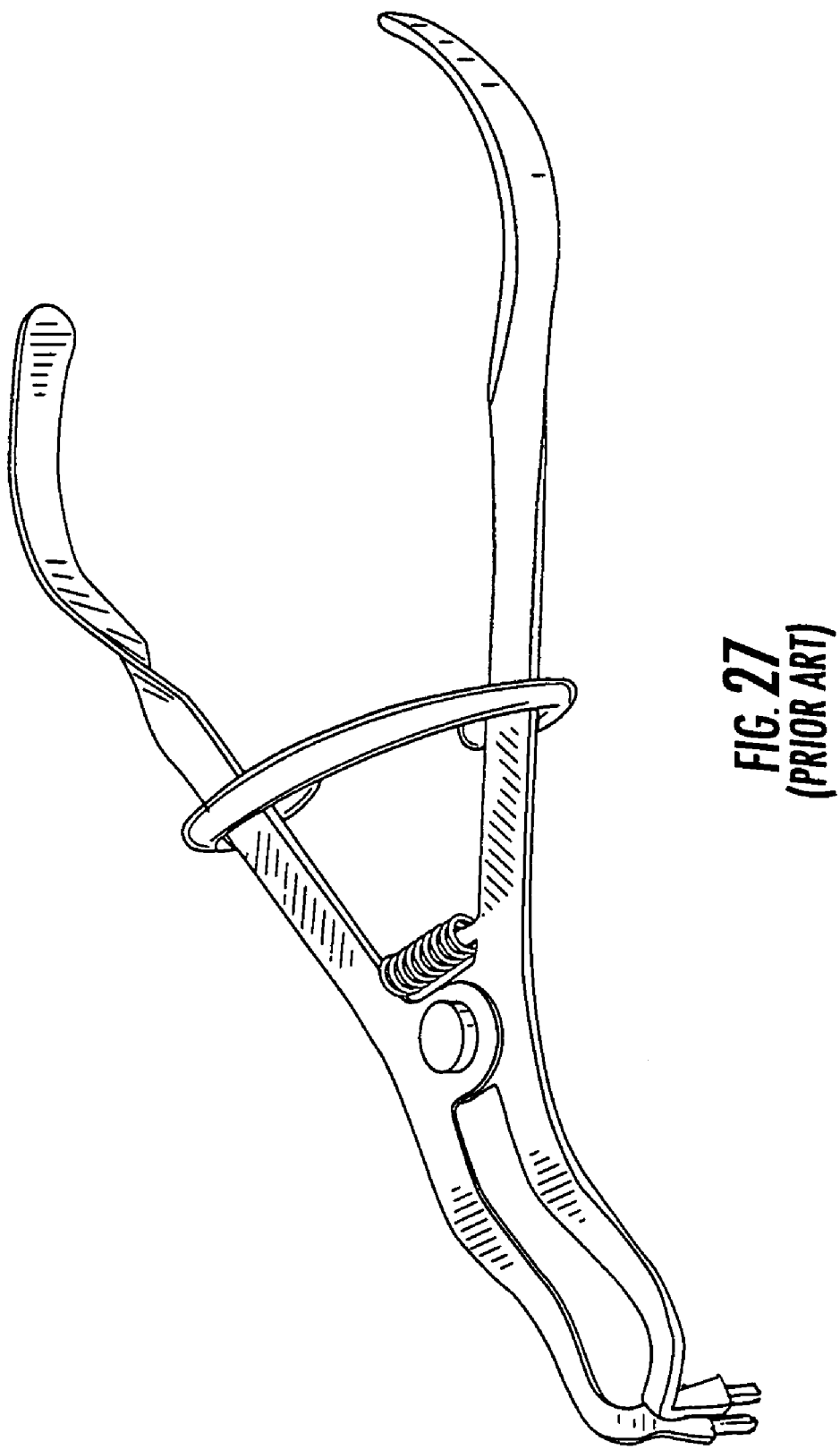
FIG. 27 is a perspective view of a prior art rubber-dam clamp forceps.
Figure 28:
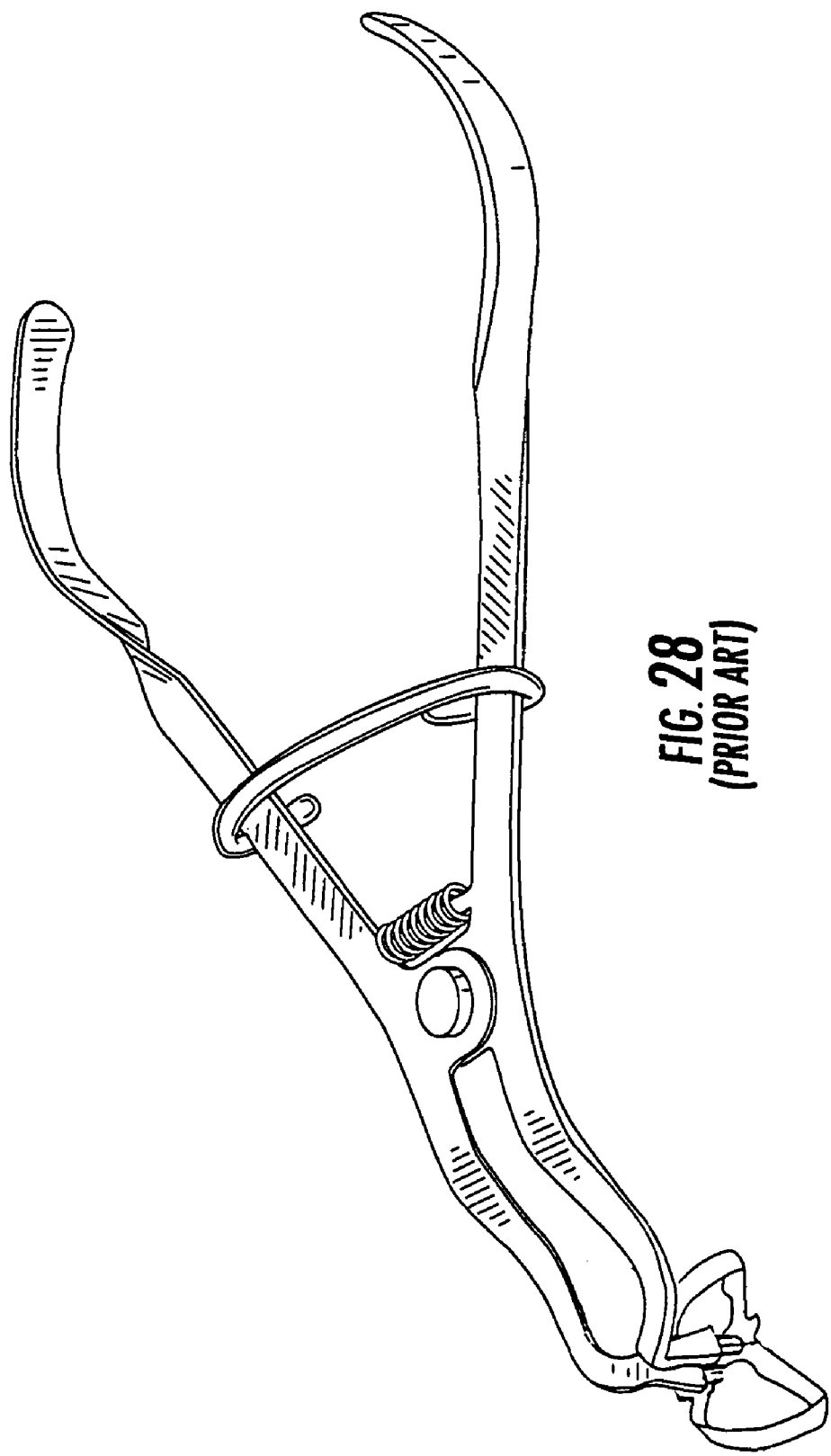
FIG. 28 is a perspective view of the prior art rubber-dam clamp forceps of FIG. 27 engaging a rubber-dam clamp.
Figure 29:
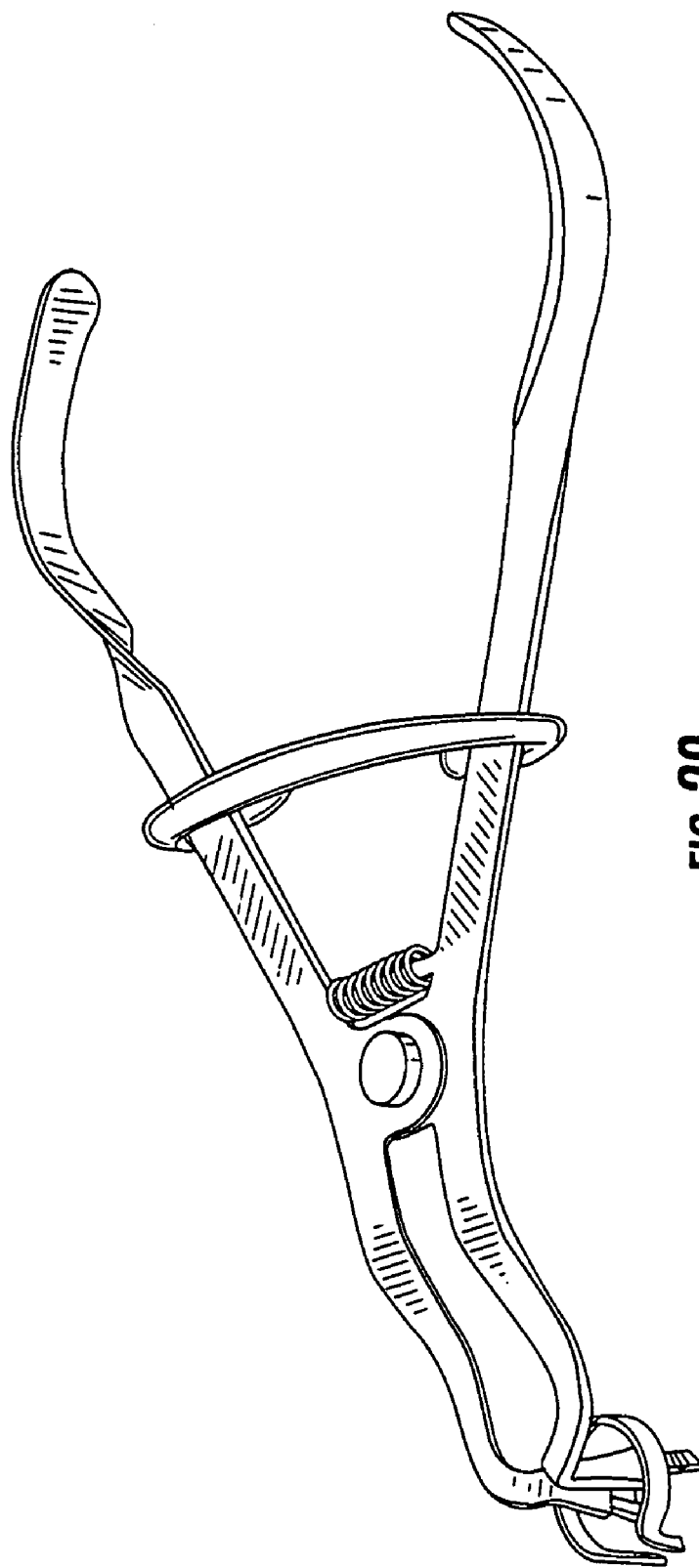
FIG. 29 is a perspective view of the prior art rubber-dam clamp forceps separating a dental retaining ring.

In the illustrated embodiment, and as best seen in FIG. 20, tines 334a and 334b are angled with respect to the C-shaped portions at an angle B in a range of about 6° to 14° and, more preferably, in a range of about 8° to 12° and, more preferably approximately 10°. Furthermore, as best seen in FIGS. 19 and 21, tines 334a and 334b are spaced inward from the ends 336a' and 336b' of seats 338a and 338b so that the lower ends or distal ends 348b and 350b of tines 334a and 334b are spaced more closely than the tines of the previous embodiments. As noted previously, the lower ends of the tines in the previous embodiments are such that they align with the openings of the rubber-dam clamp. However, is some circumstances, it is preferably that the lower ends of the tines be spaced more closely and, further, require separation of the distal portions of the dental instrument to engage the rubber-dam clamp, for example, when the dental instrument is placed around a larger tooth. It should also be understood that the spacing of the tines may be reduced even further, for example, such that the lower ends of the tines contact when the C-shaped portions 336a and 336b contact. Alternately, the spacing of the tines may be increased. For example, this may be appropriate where a patient has a hyper-erupted tooth.

While several forms of the invention have been shown and described, other forms will now be apparent to those skilled in the art. Therefore, it will be understood that the embodiments shown in the drawings and described above are merely for illustrative purposes, and are not intended to limit the scope of the invention, which is defined by the claims, which follow as interpreted under the principles of patent law including the doctrine of equivalents.

We claim:

1. A dental instrument comprising:
a first arm;
a second arm pivotally coupled to said first arm about a pivot axis, said first arm and said second arm being pivotal with respect to each other in a plane generally orthogonal to said pivot axis;
each of said arms having a proximal portion, a medial portion, and a distal portion, said proximal portions defining hand grip portions, and said arms being pivotally connected at their medial portions;
a spring biasing said distal portions of said arms toward each other;
each of said distal portions comprising a first portion and a prong portion depending from said first portion; and
said prong portions comprising back-to-back generally C-shaped portions and spaced apart tines, said C-shaped portions defining a pair of seats, said tines depending from said seats and having spaced apart distal ends adapted for engaging a rubber-dam clamp, and said seats providing contacts for a dental retaining ring.

2. The dental instrument according to claim 1, said tines each having an upper portion with a first width and a lower portion having a second width, said second width being smaller than said first width wherein said lower portions are sized to insert into openings of a rubber-dam clamp.

3. The dental instrument according to claim 2, said tines each having a groove between said upper portions and said lower portions.

4. The dental instrument according to claim 1, wherein said tines are non-orthogonal with respect to said plane.

5. The dental instrument according to claim 1, wherein said distal portions are forward of said medial portions, said tines being angled forward of said first portions of said distal portions of said arms.

6. The dental instrument according to claim 1, wherein each of said first portions includes a planar lower surface.

7. The dental instrument according to any of claim 1, wherein said tines are removably mounted to said prong portions.

8. The dental instrument according to any one of claim 1, wherein said tines are pivotally mounted to said prong portions.

9. A dental instrument comprising:
a first arm;
a second arm pivotal coupled to said first arm about a pivot axis, said first arm and said second arm being pivotal with respect to each other in a plane generally orthogonal to said pivot axis;

each of said arms having a proximal portion, a medial portion, and a distal portion, said proximal portions defining hand grip portions, and said arms being pivotally interconnected at their respective medial portions;

a spring generating a biasing force to urge said distal portions of said arms toward each other; and each of said distal portions comprising:
a prong portion, said prong portion including a first portion and a second portion, said first portions each including a seat capturing portions of a dental retaining ring, said second portions extending from said first portions and each having a distal end engaging a rubber-dam clamp, and said seats being provided inwardly of said distal ends.

10. The dental instrument according to claim 9, wherein said second portions comprise tines, each tine having an upper portion with a first width and a lower portion having a second width, said second widths being smaller than said first widths wherein said lower portions are sized to insert into openings of the rubber-dam clamp.

11. The dental instrument according to claim 10, said tines each having a groove between said upper portions and said lower portions.

12. The dental instrument according to claim 11, said tines being angled in a range of 96° to 104° with respect to said plane.

13. A dental instrument comprising:
a first arm;
a second arm pivotal coupled to said first arm about a pivot axis, said first arm and said second arm being pivotal with respect to each other in a plane generally orthogonal to said pivot axis;
each of said arms having a proximal portion, a medial portion, and a distal portion, said proximal portions defining hand grip portions, and said arms being pivotally interconnected at their respective medial portions;
a spring generating a biasing force to urge said distal portions of said arms toward each other; and
each of said distal portions comprising:
a prong portion, said prong portion including a first portion and a second portion, said first portions being adapted to capture portions of a dental retaining ring therein wherein each of said first portions is adapted to capture the ring in at least two planes wherein the retaining ring does not wok in said first portions, and said second portions extending from said first portions and each having a distal end adapted to engage a rubber-dam clamp wherein said distal ends are spaced apart when said distal portions abut.

14. The dental instrument according to claim 13, wherein said first portions include seats for capturing portions of a dental ring.

15. A dental instrument comprising:
a first arm;
a second arm pivotal coupled to said first arm about a pivot axis, said first arm and said second arm being pivotal with respect to each other in a plane generally orthogonal to said pivot axis;
each of said arms having a proximal portion, a medial portion, and a distal portion, said proximal portions defining hand grip portions, and said arms being pivotally interconnected at their respective medial portions;
a spring generating a biasing force to urge said distal portions of said arms toward each other; and each of said distal portions comprising:
a prong portion, said prong portion including a first portion and a second portion, said first portions being adapted to capture portions of a dental retaining ring therein wherein each of said first portions is adapted to capture the ring in at least two planes wherein the retaining ring does not rock in said first portions, and said second portions extending from said first portions and each having a distal end adapted to engage a rubber-dam clamp wherein each of said first portions comprises an arcuate portion, each of said arcuate portions defining a seat, and said seats capturing the portions of the dental retaining ring therein.

16. The dental instrument according to claim 15, wherein each of said arcuate portions has an apex, said apexes contacting each other when said biasing force is unopposed and said arms are urged toward each other by said spring.

17. The dental instrument according to claim 16, wherein at least a portion of each of said second portions of said prong portions are (1) removable or (2) pivotally mounted to said distal portions.

18. A dental instrument comprising:
a first arm;
a second arm pivotally coupled to said first arm about a pivot axis, said first arm and said second arm being pivotal with respect to each other in a plane generally orthogonal to said pivot axis;
each of said arms having a proximal portion, a medial portion, and a distal portion, said proximal portions defining hand grip portions, said arms being pivotally coupled at their respective medial portions;
a spring generating a biasing force to urge said distal portions toward each other; and
each of said distal portions having a first portion being configured to capture an arm of a retaining ring therein and having a second portion forming a tine extending from said first portion, each of said tines being configured to engage a rubber dam clamp, and each of said second portions being angled forward of said first portions in a direction away from said medial portions wherein said tines are non-parallel to said pivot axis, and each of said tines having a distal end, said distal ends being spaced apart when said distal portions contact each other.

19. The distal instrument according to claim 18, wherein said second portions are angled with respect to said first portion in a range of about 96° to 104°.

20. The dental instrument according to claim 18, wherein said first portions comprise arcuate portions, each of said arcuate portions being configured to capture an arm of a retaining ring therein.

21. The dental instrument according to claim 20, wherein each of said arcuate portions has an end, said tines being (1) positioned inwardly of said ends of said arcuate portions or (2) extended from said ends and being aligned with said ends of said arcuate portions.

* * * * *

UNITED STATES PATENT AND TRADEMARK OFFICE
CERTIFICATE OF CORRECTION

PATENT NO. : 7,165,970 B2  
APPLICATION NO. : 11/068367  
DATED : January 23, 2007  
INVENTOR(S) : Robert Anderson It is certified that error appears in the above-identified patent and that said Letters Patent is hereby corrected as shown below:

Column 11:
Line 47, Claim 13, "wok" should be --rock--.

Signed and Sealed this

Thirteenth Day of May, 2008

JON W. DUDAS  
*Director of the United States Patent and Trademark Office*